US012661523B2

(12) United States Patent
Schuster et al.

(10) Patent No.: US 12,661,523 B2
(45) Date of Patent: Jun. 23, 2026

(54) REAL TIME MONITORING OF COSMETIC LASER AESTHETIC SKIN TREATMENT PROCEDURES

(71) Applicant: LUMENIS LTD., Yokneam (IL)

(72) Inventors: Israel Schuster, Kiryat Tivon (IL); Andrey Gandman, Haifa (IL)

(73) Assignee: LUMENIS BE LTD., Yokneam (IL)

( * ) Notice: Subject to any disclaimer, the term of this patent is extended or adjusted under 35 U.S.C. 154(b) by 278 days.

(21) Appl. No.: 17/226,235

(22) Filed: Apr. 9, 2021

(65) Prior Publication Data

US 2021/0220667 A1      Jul. 22, 2021

Related U.S. Application Data

(63) Continuation of application No. PCT/IL2019/051091, filed on Oct. 7, 2019.
(Continued)

(51) Int. Cl.
*A61N 5/06* (2006.01)
*A61N 5/067* (2006.01)

(52) U.S. Cl.
CPC .... *A61N 5/0616* (2013.01); *A61N 2005/0627* (2013.01); *A61N 2005/0651* (2013.01); *A61N 2005/0658* (2013.01); *A61N 5/067* (2021.08)

(58) Field of Classification Search
CPC .................. A61N 5/0616; A61N 5/067; A61N 2005/0627; A61N 2005/0651;
(Continued)

(56) References Cited

U.S. PATENT DOCUMENTS 6,758,845 B1    7/2004  Weckwerth et al.
7,029,469 B2 *  4/2006  Vasily .................. A61B 18/203
                                                    606/9
(Continued)

FOREIGN PATENT DOCUMENTS

WO       WO-02094117 A1 *  11/2002  ............. A61B 18/20
WO       2017183825       10/2017

OTHER PUBLICATIONS

Search Report—corresponding PCT Application No. PCT/IL2019/051091, dated Dec. 4, 2019, 4 pages.

*Primary Examiner* — Michael T. Holtzclaw
(74) *Attorney, Agent, or Firm* — ISUS INTELLECTUAL PROPERTY PLLC; Anthony Jason Mirabito

(57) ABSTRACT

A cosmetic method of treating skin tissue with a source of treatment light includes providing a source of treatment light along an optical axis; providing one or more sources of illumination light along the optical axis; providing one or more sensors along the optical axis; providing a programmable controller, the programmable controller controlling the activation of the source of illumination light and the source of treatment light. The method includes the steps of: the controller activating the one or more sources of illumination light and directing it to the skin tissue, the one or more sensors measuring the light reflected from the skin tissue and transmitting information sensed of measured light to the programmable controller; the programmable controller processing the measured light received from the output of the one or more sensors and providing a treatment light regimen; the programmable controller activating the source of treatment light according to the treatment regimen to the skin tissue; and, treating the skin tissue.

22 Claims, 19 Drawing Sheets

Related U.S. Application Data

(60) Provisional application No. 62/744,219, filed on Oct. 11, 2018.

(58) Field of Classification Search
CPC .......... A61N 2005/0658; A61N 5/0617; A61N 2005/0626; A61B 2018/00452; A61B 2018/00458; A61B 2018/0047; A61B 2018/00476; A61B 2018/00636; A61B 2018/00904; A61B 18/203; A61B 5/441; A61B 2018/20361
See application file for complete search history.

(56) References Cited

U.S. PATENT DOCUMENTS

| | | | |
|---|---|---|---|
| 2003/0036751 A1 | 2/2003 | Anderson et al. | |
| 2008/0058782 A1 | 3/2008 | Frangineas et al. | |
| 2008/0154248 A1* | 6/2008 | Dunki-Jacobs | A61B 18/203 606/9 |
| 2010/0185064 A1* | 7/2010 | Bandic | A61B 5/444 600/306 |
| 2012/0289885 A1* | 11/2012 | Cottrell | A61N 5/0616 604/20 |
| 2013/0345685 A1* | 12/2013 | Poran | A61B 18/20 606/9 |
| 2016/0324586 A1 | 11/2016 | Zingaretti et al. | |
| 2018/0303406 A1* | 10/2018 | McKinney | A61B 5/0082 |
| 2019/0117307 A1* | 4/2019 | Lee | A61N 5/0616 |
| 2019/0142512 A1* | 5/2019 | Chen | A61N 5/06 606/9 |
| 2019/0274759 A1* | 9/2019 | Royon | A61N 5/0616 |
| 2020/0179713 A1* | 6/2020 | Subhash | A61B 5/0077 |

* cited by examiner

704

700

816

817

818

800

Probing illumination

Untreated area

Treated zone:
Coagulation

Rayleigh Scattering          Mie Scattering          Mie Scattering
                                                    larger particles Direction of incident light Comea (face)
Crystalllne cone
Upper iris cells
Matrix cells of cornea
Lower iris cells
Sensory cells
Rhabdom 212
Fast photodiode
Optical guide
Micro-lens

210

220
222

REAL TIME MONITORING OF COSMETIC LASER AESTHETIC SKIN TREATMENT PROCEDURES

RELATED APPLICATIONS

This application is a continuation of PCT/IL2019/051091, filed Oct. 7, 2019, which is related to U.S. Provisional Application No. 62/728,096, filed Sep. 7, 2018, and U.S. Provisional Application 62/744,219, filed Oct. 11, 2018, both bearing the title "Real Time Monitoring of Laser Treatment Procedures", the entire contents of both of which are herein incorporated by reference and to which priority is claimed to U.S. Provisional Application 62/744,219, filed Oct. 11, 2018. This application is also related to U.S. Provisional Application No. 62/754,730, filed Nov. 11, 2018, entitled "Automation of Apparatus and Methods of Aesthetic Skin Treatments", the entire contents of which is herein incorporated by reference.

BACKGROUND OF THE PRESENT INVENTION

To date, the laser-based aesthetic treatments paradigm is mostly completely manual and highly user dependent, leaning heavily on the practitioner's subjective assessment of a subject's skin and target physical properties. However, the implementation of technology elements that may shift the existing manual paradigm to an automated, more scientific and user-independent mode may be feasible. It has strong scientific rational considering the principles of aesthetic medical laser treatments and the physics of laser-tissue interaction.

It is believed that companies in the aesthetic skin tissue treatment industry have much less experience with some of the key elements of adapting largely manual systems and methods to new technologies, (i.e. computer vision, image processing, artificial intelligence (AI) and robotics, including robotic maneuverability, imaging and/or sensing elements).

A body of data, know-how and experience with creating and validating effective linkage between certain target skin/lesion/hair properties and laser settings already exists. This body of knowledge has, for example, in the M22 laser system made and sold by Lumenis Ltd, the assignee of the present invention and application, been incorporated into certain "presets" for laser settings. Thus, an operator selecting a certain preset sets into motion a treatment that may well have been developed from experience over a number of years for providing treatments for a certain purposes, by manipulating such things as pulse width, power setting, number of pulses, wavelength(s) of laser provided, etc.

However, these presets are implemented under the control of the operator in accordance with the operator's own subjective judgment of the person's skin type and target lesion properties. Thus, creating a linkage between certain target properties and the required laser setting is practically feasible (though currently not personalized and not automatic).

In developing the present invention, an analysis and conceptual design to assess what technologies and methods may be integrated with medical laser platforms was undertaken to achieve automatic, on-board, real-time skin diagnostic and personalized computing of the laser settings that would remove the dependency in operator subjective inputs and provide the optimal clinical outcomes.

Moreover, such a real time system may be used in conjunction with a completely hands-free medical laser "robotic" platform for applications that require high spatial accuracy (e.g. multiple small pigmented birthmarks or moles on the skin) and/or tedious coverage of large surface areas (e.g. hair removal or tattoos removal) was developed.

It is envisioned that the next generation platform will likely consist of a therapeutic laser module, a new skin diagnostic module with a smart algorithm for computing the required laser setting, a new robotic module that will control and maneuver the laser applicator over the targeted area while considering safety and efficiency, and a new user interface that will allow the user to plan/mark the desired treatment area.

The technical feasibility of integrating robotic capabilities to allow for hands-free procedures is partially proven as robotic technology has been commercialized in variety of applications, including medical ones. There are several commercial products in the health market which are based on robotics capabilities. For example, Mazor Robotics provides such technology in the Da Vinci® surgery system.

Conducting automatic skin diagnostic and mapping of the key chromophores (e.g. using multispectral reflectance imaging, visual analysis) has been proven, based on theoretical analysis and by range of commercially available portable devices that use similar principles, although each device is believed limited to a certain number of skin parameters, work off-line and is not integrated into a laser platform.

The technical feasibility of computing optimal laser settings based on, for example, skin diagnostic measurements of key chromophores, is partially proven as the entire theory behind selective laser treatment has been extensively explored in the past 20 years using skin models which have been validated in clinical studies. In today's practice, the implementation of this knowledge is through "presets" that are part of the system's user interface, though they are completely dependent on proper judgment of target properties and manual selection by the user.

The technical feasibility of seamless integration of skin diagnostic technologies with medical laser platform and closing the loop in real-time to determine the optimal laser setting, with smooth interface to procedure workflow is yet to be proven and is a key design of the present invention.

BACKGROUND OF AESTHETIC TREATMENT AND TYPES

Ultimately, although current aesthetic laser treatments do work, they are, as mentioned, highly user dependent, often unpredictable, take a long time, are costly (due, for example, to the need for multiple passes and office visits) and have a varied incidence of complication. In general, a practitioner visually examines the subject patient, the region of the body of interest, sometimes interviews the subjects to learn their typical skin reaction to exposure to the sun. The practitioner next may manually select the laser parameters either directly or through a "preset" user interface, and then may fire a test patch to analyze the skin's response to determine whether the settings just made are acceptable or not.

Then, the practitioner continues with the treatment, covering the entire surface area with a sometimes tedious, step by step, application of laser firings, creating at times issues of missed coverage or overlapping coverage producing sometimes undertreatment or overtreatment respectively. If the laser setting is too weak, there may be undertreatment and a need to repeat with additional passes (i.e. additional visits), raising the overall burden and cost of the treatment. If the laser setting is too aggressive, there may be overtreatment, leading to undesired adverse events such as temporary pain, blisters and burns in various degrees, hypo/hyper pigmentation, scarring and purpura (bleeding).

The rapidly growing market of aesthetic treatments solely relies on the experience of a trained physician (i.e., dermatologists). The physician usually possesses the knowledge about the specific skin lesion, its classification, composition and structure. However, only some physicians possess a complete knowledge about laser-tissue interaction, which is essential in setting the optimal laser parameters for safe and effective clinical outcomes. There are growing segments in the market of users who are lower-level practitioners and who lack the required knowledge (i.e., non-dermatologist MDs, laser technicians, nurses or cosmeticians). Moreover, treatments typically are manual and tedious. The practitioner may visually aim a laser handpiece at the treatment position and deliver the laser pulse manually. The practitioner may need to repeat this operation to cover the entire treatment area spot-by-spot or by gliding the handpiece in the case of a continuous laser emission. This manual operation is tiresome, and it is difficult to control the treatment quality in terms of coverage, overlapping and repetitions.

Much of the knowledge about the specifics of laser treatments (type of laser, pulse duration, frequency and fluence) is transferred from the laser manufacturer to the practitioner through a user manual with general guidelines and software presets. The problems with these presets is that: (1) they are dependent on the subjective judgment of skin target properties by the practitioner; (2) although they may have been tested on various skin types, the actual variety of skin types is much larger, with the consequence that the proposed settings may not be optimal to the person/body area about to be treated; and (3) they do not consider the actual physical features of the tissue such as the exact target diameter. The need for more robust way of personalized skin analysis and tailored treatment regimen is thus evident.

As the aesthetic market is so diversified in type of practitioners (ranging from professional dermatologists to cosmeticians) and lacks clear quality assurance measures, it may be difficult to obtain clear quantification on how many treatments a patient could have been spared if the practitioner had used the optimal setting, or, how much better the clinical outcomes could have been. Examples of types of treatment follow.

Hair Removal

For hair removal, while the typical number of hair removal treatments required for satisfactory results may be expected to be in the range of 6 or so, in practice a higher number of treatments are often required. The reasons are not well documented and are multifactorial. However, based on experience, they correlate with suboptimal adjustment of the laser parameters and/or suboptimal manual coverage of the treated surface area. The former is an outcome of subjective assessment of skin and hair type that leads to suboptimal laser setting, and the latter is subject to the need to cover large surface area (1000-2000 cm$^2$) with lasers having a small spot size (~3×3 cm at best) with difficulties of controlling quality in terms of coverage, overlapping and repetitions.

Overlapping laser firings may well create additional issues. It is not only inefficient in terms of time; it also creates excessive pain (due to overheating) in the area of the overlapping treatments. It is currently a manual, tedious task and takes a typical time slot of 30 minutes to complete a single treatment. Moreover, the hair removal market has expanded far beyond professional users to cosmeticians, for example, where the cosmetician's ability to accurately determine the skin and hair properties and thus the appropriate laser setting may be inferior to that of a professional. This, in turn, exposes the subjects to a significantly higher rate of unsatisfactory procedures and adverse outcomes. Another growing market is home use devices for hair removal. In this segment, users have no knowledge at all for selecting the optimal parameters, and thus the device manufacturers must compromise on efficacy for the sake of safety. A technology that has the ability to scan the skin/hair and deduce the optimal parameters that should be used for safe and satisfactory results may be highly beneficial.

Tattoo Removal

In tattoo removal, the challenges are twofold. First, in order to destroy tattoo ink selectively, the best laser wavelength should be chosen to achieve selective absorption for the particular ink color or colors while minimizing nonspecific effects. However, commonly used tattoo inks are very little regulated, and this ink composition is highly variable. As a result, what appear to be similar ink colors may have wide peak absorption range and the practitioner has no way to determine the exact type/properties of the specific ink and thus the optimal laser wavelength that should be used.

Moreover, in addition to the ink's color properties, the skin type (amount of melanin), the depth of the ink and the amount should also be considered for optimal laser setting and clinical outcomes. Today, this entire process is done by the practitioners based on their personal experience (or lack of it!) and subjective assessments. Secondly, the tattoo surface area is often very large, as large as the whole hand, chest or back. In such cases, the practitioner may manually treat surface areas as large as 1200 cm$^2$ with a laser hand piece that has spot size of ~1 cm$^2$. This process is time consuming and tedious. In tattoo removal, the reported average number of treatments is usually 6-10, but 15-20 treatments or more is not an unusual. The reasons are probably multifactorial, but using suboptimal settings is certainly a key factor.

Vascular Removal

To selectively destroy vascular lesions and veins, the practitioner may need to determine the depth and diameter of the target (and of course the skin type). Today, there is no means other than subjective assessment of the size and depth. The operator may use available portable illumination devices that may emphasize the veins, but, it does not offer quantification of any parameters which are important for an effective laser treatment. The selection of laser parameter is complex. Wavelength (WL) selection is an important parameter that may determine the tissue effect. Ideally, the ratio of absorption of the vascular target vs. normal surrounding skin should exceed 10:1. Because epidermal pigment overlies the vessel, WL selection should be based on optimal ratios of vascular to pigment destruction. Pulse duration is another important parameter in limiting the thermal effects to within the target vessel and is affected by the vessel sizes. With longer pulses (6-40 ms), intravascular thrombosis and spot-sized purpura are mitigated as gentle heating resulted in vessel wall stenosis and thrombosis of the larger vessels, but not the micro vessels that produce widespread purpura. Spot size is also important and should be considered carefully together with fluence as larger spot may produce more epidermal damage and pain[6].

Pigmented Lesions

In order to selectively destroy pigmented lesions, the practitioner may need to determine lesion type, skin type, the lesion's density of melanin, and the depth of the lesion e.g. is it epidermal, junctional or dermal. Again, this entire process is done manually, or by using available portable tools, and it relies entirely on the practitioner's knowledge and professionalism to choose the correct treatment. To effectively treat pigmented lesions, one should be familiar with histopathological characteristics of the lesion.

With this knowledge, the lesion depth can be determined (i.e., epidermal, dermal, or combination of both) and then the most suitable laser setting can be decided upon. Sample rules for laser selection are as follows: benign pigmented lesions located more superficially can be treated with the shorter wavelength e.g. 532 nm, but deeper lesions may well require longer wavelengths, such as 1064 nm, for better depth penetration. Larger spot sizes also enhance the penetration depth. Pigmented lesions with atypical features (e.g., asymmetry, border, color) are examples of lesions that likely should not be treated with a laser. Unfortunately, pigmented lesions respond variably to lasers, and for any individual it is difficult to predict the treatment outcome. The reasons are surely multifactorial, but the subjective laser selection can certainly play a notable role in this.

Adverse Effects (Safety)

The following data describes the common Adverse Effects (AE) correlated with current manual aesthetic laser treatments: In meta-analysis (Shen L., Zhou G, Zhao J, Li P, Xu Q, Dong Y, Zhang Z. *Pulsed dye laser therapy for infantile hemangiomas: a systemic review and meta-analysis. QJM.* 2015 June; 108(6): 473-80), and large-scale reviews the adverse events (AE) occurrence in veins (Hemangioma) treatment is overall 6.3%. In another study for pigmentation (Melasma) (Halachmi S, Haedersdal M, Lapidoth M. *Melasma and laser treatment: an evidenced-based analysis. Lasers Med Sci.* 2014 March; 29(2): 589-98) AE reaches as high as 13.3% worsening, 17% hyperpigmentation, 6% blistering and 4% crusting.

The FDA MAUDE (*FDA MAUDE Data on Complications with Lasers, Light Sources, and Energy-Based Devices*; Anne Marie Tremaine, MD and Mathew M. Avram, MD; *Lasers in Surgery and Medicine* 47:133-140 (2015)) data on complications with light sources database reported cases between 1994-2013, there are more than 1200 Medical Device Reporting (MDRs) (e.g. 690 burn and blisters, 155 scarring, and 147 dyschromia). The authors concluded there that laser hair removal is the most common indication associated with AEs and the most common AEs seen across all devices are blisters and burns, following by scarring, dyschromia and atrophy of the skin.

In most cases, after investigation, the manufacturers determined the AE is likely to be due to operator error including inappropriate settings. In fact, the actual numbers are most probably much higher as many physicians may have never reported AEs to the FDA. It well may be that AE in aesthetic procedures by non-physician operators is higher than for physician operators.

Most importantly, a clear trend demonstrates a dramatic increase in the number of lawsuits associated with non-physician operators' (NPO) performance of laser surgery. The NPOs comprise a vast diversity of operators, including nurse practitioners, registered nurses, medical assistants, and aestheticians, among others. One study (Jalian H R, Jalian C A, Avram M M. *Increased risk of litigation associated with laser surgery by nonphysician operators. JAMA Dermatol.* 2014 April; 150(4): 407-11) tracked 175 legal cases from 1999 to 2012 involving injuries from cutaneous laser surgery. During this time period, 75 (43%) involved a non-physician operating a laser, increasing from 36% in 2008 to 78% in 2012.

SUMMARY OF THE PRESENT INVENTION

In an aspect, a cosmetic method of treating skin tissue with a source of treatment light includes providing a source of treatment light along an optical axis; providing one or more sources of illumination light along the optical axis; providing one or more sensors along the optical axis; providing a programmable controller, the programmable controller controlling the activation of the source of illumination light and the source of treatment light. The method includes the steps of: the controller activating the one or more sources of illumination light and directing it to the skin tissue, the illumination light being reflected from the skin tissue along the optical axis to the input of the one or more sensors; the one or more sensors measuring the light reflected from the skin tissue and transmitting information sensed of measured light to the programmable controller from the output of the one or more sensors; the programmable controller processing the measured light received from the output of the one or more sensors and providing a treatment light regimen; the programmable controller activating the source of treatment light according to the treatment regimen to the skin tissue; and, treating the skin tissue. In another aspect, the method may further comprise providing light directing elements to direct both the source of treatment light and the source of illumination light along the optical axis.

In a further aspect, the source of illumination light may be a plurality of light sources having different wavelengths of light output; the method further comprises the step of the controller selecting one or more of the plurality of different light source wavelengths and activating the one or more light sources to illuminate the skin tissue. The plurality of light sources are LED light sources. Further, the LED light sources have wavelengths in the range of 400 nm to 900 nm. Yet further, the treatment light source is selected from one or more of: a fiber laser source, a solid-state laser source, an Intense Pulse Light (IPL) light source, and a LED light source. The skin tissue is treated for one or more categories of: pigmented lesions, vascular removal, tattoo removal, and hair removal.

In yet another aspect, the method may further comprise the step of the controller selectively activating one or more of the one or more LED light sources dependent upon the category of skin tissue treatment. Further, activating one of the one or more sources of illumination light may be dependent on the depth within the skin tissue. The method may further comprise the step of reactivating the one or more sources of illumination light after the step of treating the skin tissue to determine the conditions of the skin tissue after treatment.

In yet a further aspect, the step of the programmable controller processing the measured light received from the output of the one or more sensors and providing a treatment light regimen includes the step of analyzing the information by matching the information to information contained in a lookup table in a memory associated with the programmable controller, and selecting a treatment regimen based on a match in the lookup table. In addition, the step of the programmable controller processing the measured light received from the output of the one or more sensors and providing a treatment light regimen includes the step of analyzing the information by matching the information to information contained in one or more embedded algorithms contained in a memory associated with the programmable controller, and selecting a treatment regimen based on a match. Further, the step of the programmable controller processing the measured light received from the output of the one or more sensors and providing a treatment light regimen includes the step of analyzing the information by matching the information to information using artificial intelligence methods and deep learning contained in a memory associated with the programmable controller, and selecting a treatment regimen based on a match.

In an aspect, an apparatus for treating skin tissue with a source of treatment light includes: a source of treatment light along an optical axis; one or more sources of illumination light and sensors along the optical axis; a programmable controller, the programmable controller controlling the activation of the source of illumination light and the source of treatment light; the apparatus further includes: the controller being configured to activate the one or more sources of illumination light and directing it to the skin tissue, the illumination light being reflected from the skin tissue along the optical axis to the input of the one or more sensors; wherein the one or more sensors measure the light reflected from the skin tissue and transmit information sensed of measured light to the programmable controller from the output of the one or more sensors; the programmable controller further being configured to process the measured light received from the output of the one or more sensors and provide a treatment light regimen; the programmable controller being configured to activate the source of treatment light according to the treatment regimen to the skin tissue to treat the skin tissue.

In another aspect, the apparatus further includes light directing elements to direct both the source of treatment light and the source of illumination light along the optical axis. The source of illumination light comprises a plurality of light sources having different wavelengths of light output; and wherein the controller is configured to select one or more of the plurality of different light source wavelengths and activate the one or more light sources to illuminate the skin tissue. Further, the plurality of light sources are LED light sources; the LED light sources have wavelengths in the range of 400 nm to 900 nm.

In a further aspect, the treatment light source is selected from one or more of: a fiber laser source, a solid-state laser source, an Intense Pulse Light (IPL) light source, and a LED light source. Further, the skin tissue is treated for one or more categories of: pigmented lesions, vascular removal, tattoo removal, and hair removal.

In an aspect, the controller may be configured to selectively activate one or more of the one or more LED light sources dependent upon the category of skin tissue treatment. Further, the controller may be configured to activate one of the one or more sources of illumination light dependent on the depth within the skin tissue. The controller may be configured to reactivate the one or more sources of illumination light after treatment of the skin tissue to determine the conditions of the skin tissue after treatment.

In yet a further aspect, the programmable controller processing the measured light received from the output of the one or more sensors and providing a treatment light regimen includes the step of analyzing the information by matching the information to information contained in a lookup table in a memory associated with the programmable controller, and selecting a treatment regimen based on a match in the lookup table.

In another aspect, the programmable controller is configured to process the measured light received from the output of the one or more sensors and provide a treatment light regimen includes the controller being configured to analyze the information by matching the information to information contained in one or more embedded algorithms contained in a memory associated with the programmable controller, and then being configured to select a treatment regimen based on a match.

In yet another aspect, the programmable controller is configured to process the measured light received from the output of the one or more sensors and provide a treatment light regimen includes the controller being configured to analyze the information by matching the information to information using artificial intelligence methods and deep learning contained in a memory associated with the programmable controller, and then being configured to select a treatment regimen based on a match.

DETAILED DESCRIPTION OF THE PRESENT INVENTION

Based on the discussion above, the present invention is directed to provide a system and method to perform real time monitoring of laser treatment procedures, thus paving the way in an effort towards automation of aesthetic medical laser platforms. The goal desired is a complete end-to-end solution that expands the currently available commercial offerings to include the automatic setting of laser parameters.

The end desired solution is a hands-free automated platform that will support planning and automatic execution of treatment, while the system continuously self-determines, in real-time, the appropriate laser setting and the next moves at each specific anatomical target.

In such a system, the practitioner may merely provide, via designated GUI, the clinical diagnosis and objective, the desired area(s) of treatment, "no-fire" zones and similar parameters. The system may be designed to determine the laser parameters before each laser firing and to monitor the treatment process on-line, providing a closed loop feedback to the laser system to adjust, as required, treatment parameters for optimal clinical outcomes. The likely targeted aesthetic markets for such a system are vascular and pigmented lesion treatments, hair removal, and tattoo removal.

The present invention may be integrated into an image guided autonomous robotic system, such as that which is described in U.S. Provisional Application No. 62/754,730, filed Nov. 2, 2018, the entire contents of which is incorporated herein.

Figures 1, 2:
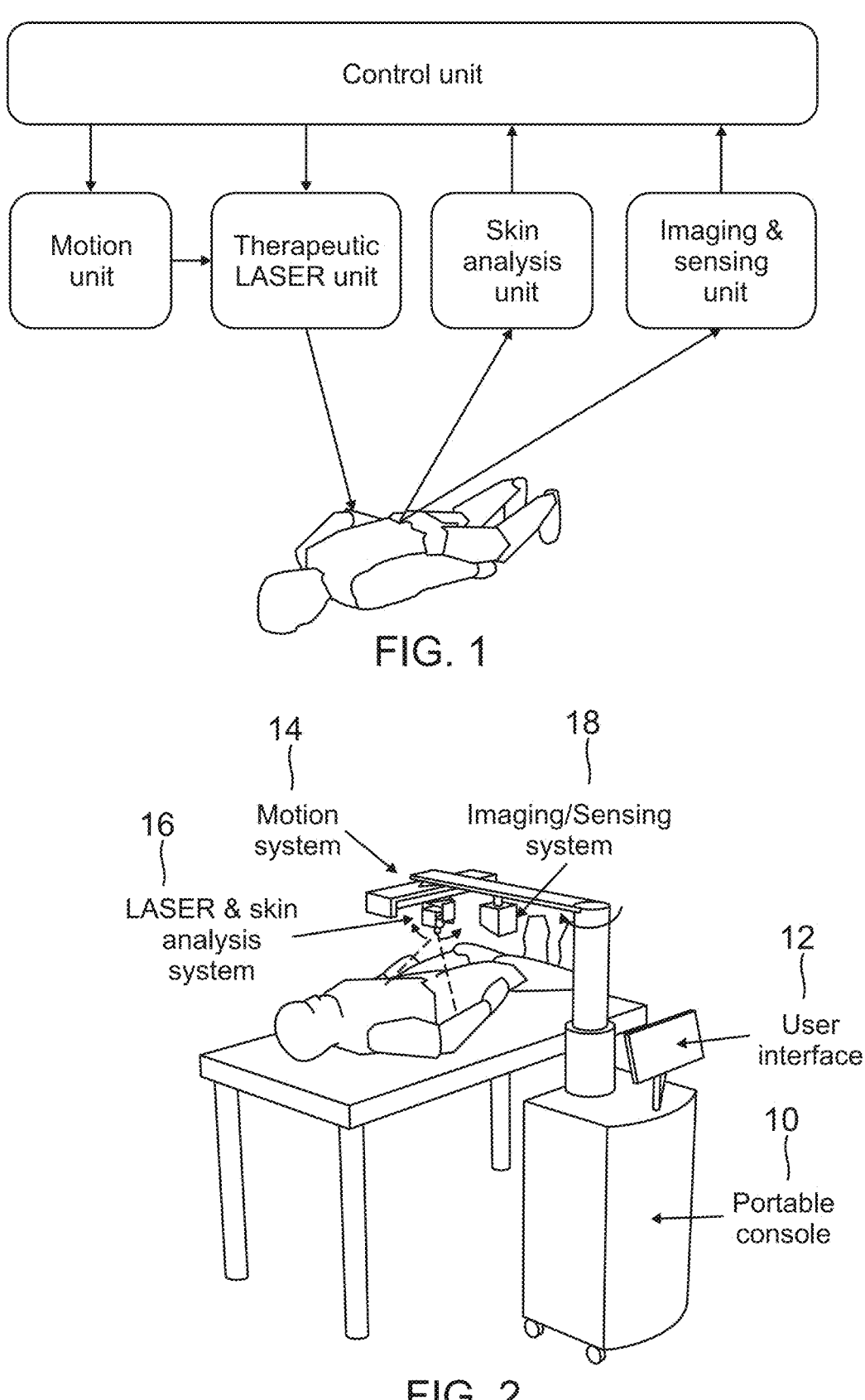
FIG. 1 illustrates a high-level functional architecture scheme of the present invention.
FIG. 2 illustrates a conceptual illustration of a hands-free automated laser medical treatment device.

The suggested system may include a console/control unit 10, a user interface 12, a motion unit 14, a laser and skin analysis system 16 and an imaging and sensing module 18, as may be seen in FIG. 2.

The console/console unit 10 may be installed in the form of a portable laser console, which preferably will be compact, low weight, low cost and low power consumption in order to be compliant with existing clinics infrastructures, workflow and economical models.

The system may capture the treatment areas on the patient and track movements in real time using an imaging/sensing sub system. From the obtained data, the system may be able to recognize the treatment regions-of-interest (ROI) and to segment them into treatment spots. The system then could guide the laser beam to the treatment region using the motion unit, and then scan the treatment region with the laser beam perpendicular to the scanned patient's surface. The laser could have a collimated and long-focal-length beam with variable spot size in order to eliminate the need to closely track human body curvatures, and by that to enable faster and simpler operation of the motion system.

In addition to the macro level planning, execution and control, the system may perform, at the treatment target location, real time skin diagnostic and monitoring and adjust the laser parameters continuously, using embedded algorithms and artificial intelligence methods.

At a high level, the technology may be based on a fast-multi-spectral reflectance/scattering imaging device integrated within a treatment laser handpiece and platform, as discussed in incorporated 62/764,730, filed Nov. 2, 2018.

Reflectance images from skin tissue is determined by two physical properties, chromophore absorption and reduced scattering of the induced illumination. Integration of those parameters through tissue depth yields the reflectance image. Thus, reflectance imaging (different wavelengths, polarizations, and patterns) provides information about the basic skin optical properties up to several millimeters in depth.

This configuration may well allow monitoring of the tissue condition before, during and after the treatment and determine, in real time, the optimal laser settings. The treatment laser firing time period is short, and thus the sensing and decision-making system will desirably also be fast, i.e. capable of delivering feedback signals in less than few milliseconds.

Thus, the present invention is designed to provide a seamless integration of automation and imaging technologies with an aesthetic medical laser system that uses advanced computational methods and algorithms to take the guesswork and manual operation out of aesthetic treatments. Instead of leaning heavily on the experience (or lack thereof) of a trained physician, their subjective assessments, personal bias, and tedious work, the present invention may provide a hands-free system that plans and treats automatically the entire surface area based on scientific quantification of the target properties and smart computation of optimal laser setting. This innovative technology may have the potential to improve clinical outcomes, reach satisfactory results in shorter time and require fewer office visits, reduce the AE rate especially when the system is operated by lower level operators, improve the economic model and, finally, increase patient satisfaction.

Technology of the Present Invention

Figure 3:
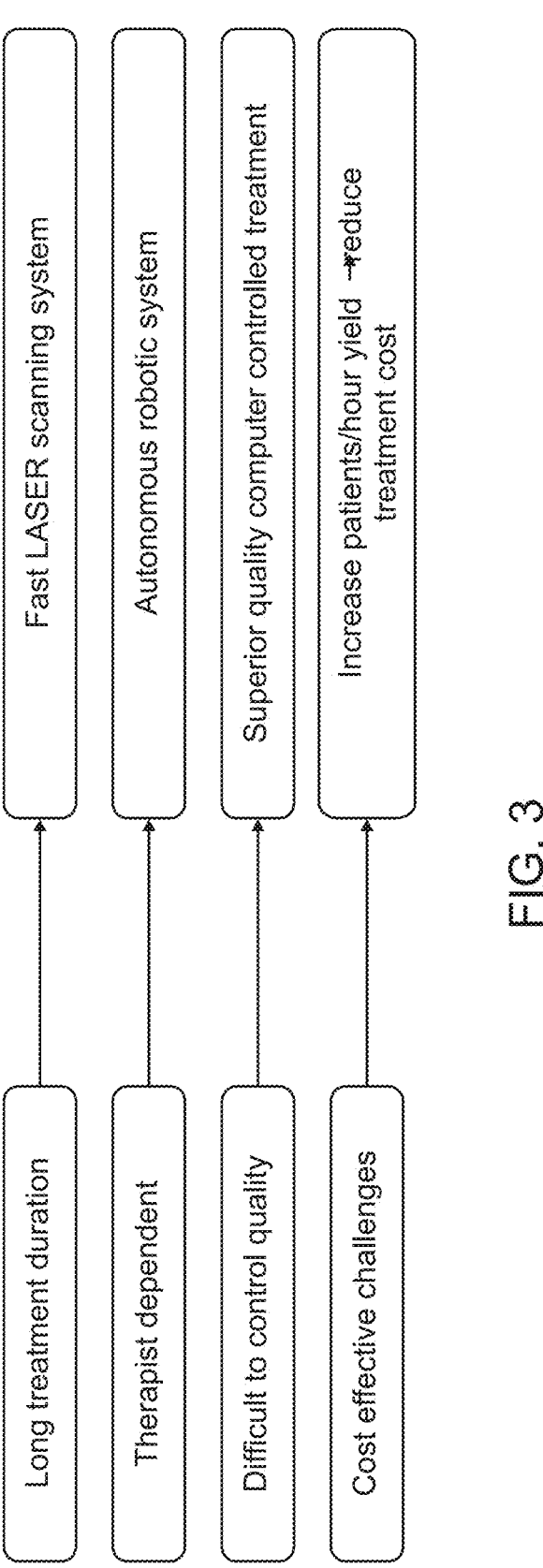
FIG. 3 illustrates current treatment issues and proposed solutions in the present invention.

FIGS. 1 through 3 illustrate, respectively, a high-level system functional architecture of technology to be implemented, a conceptual illustration of a hands-free automated laser treatment system, and an illustration of current paradigm pitfalls in present treatment regimens and proposed solutions.

Figure 4:
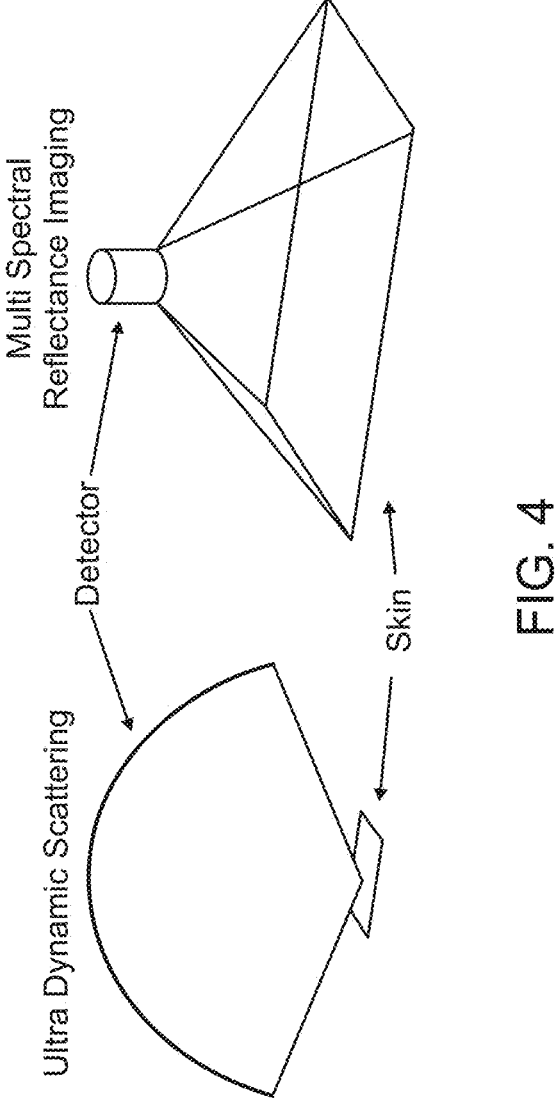
FIG. 4 illustrates conceptual differences between ultrafast dynamic scattering and multi-spectral reflectance imaging.

The envisioned automated medical laser platform may comprise technologies within the following modules, to be discussed below:
1. Skin diagnostics
  1.1 Dynamic multi spectral reflectance imaging (e.g. based on CMOS)
  1.2 Real time monitoring of laser treatments using ultra-fast dynamics scattering-photodiodes based
1. Skin Diagnostics Two different approaches for skin diagnostic, Multi Spectral Reflectance Imaging based on image sensor and Ultrafast Dynamic Scattering based on photodiodes array are described herein. While both rely on the collection of reflected light from tissue surface, they have different attributes, development risks and potential pros and cons related to a range of potential products and applications. The conceptual differences are shown in FIGS. 4A and 4B.

While the Reflectance Imaging technique (FIG. 4B) uses a camera to collect the optical signal from its field of view (FOV) with a relatively narrow angular divergence, Dynamic Scattering (FIG. 4A) provides almost a half-sphere solid angle of collection from a relatively small area. While the former can give a good spatial information about the target area, the latter is much more sensitive to treatment induced changes. Moreover, both the sampling rate and the dynamic range of single pixel (photodiode) detectors is much higher compared to imaging devices, allowing the tracking of subtle changes in scattering at GHz rate. On the other hand, imaging devices such as that shown in FIG. 4A, although they may be inferior, could provide some degree of flexibility and compromise their resolution to increase the sampling rate. Since personalization and optimization of laser treatment parameters would require both spatial and dynamical information, both technologies may be considered for feasibility.

1.1 Image Sensor Based Dynamic Multi Spectral Reflectance Imaging

Figures 5, 6:
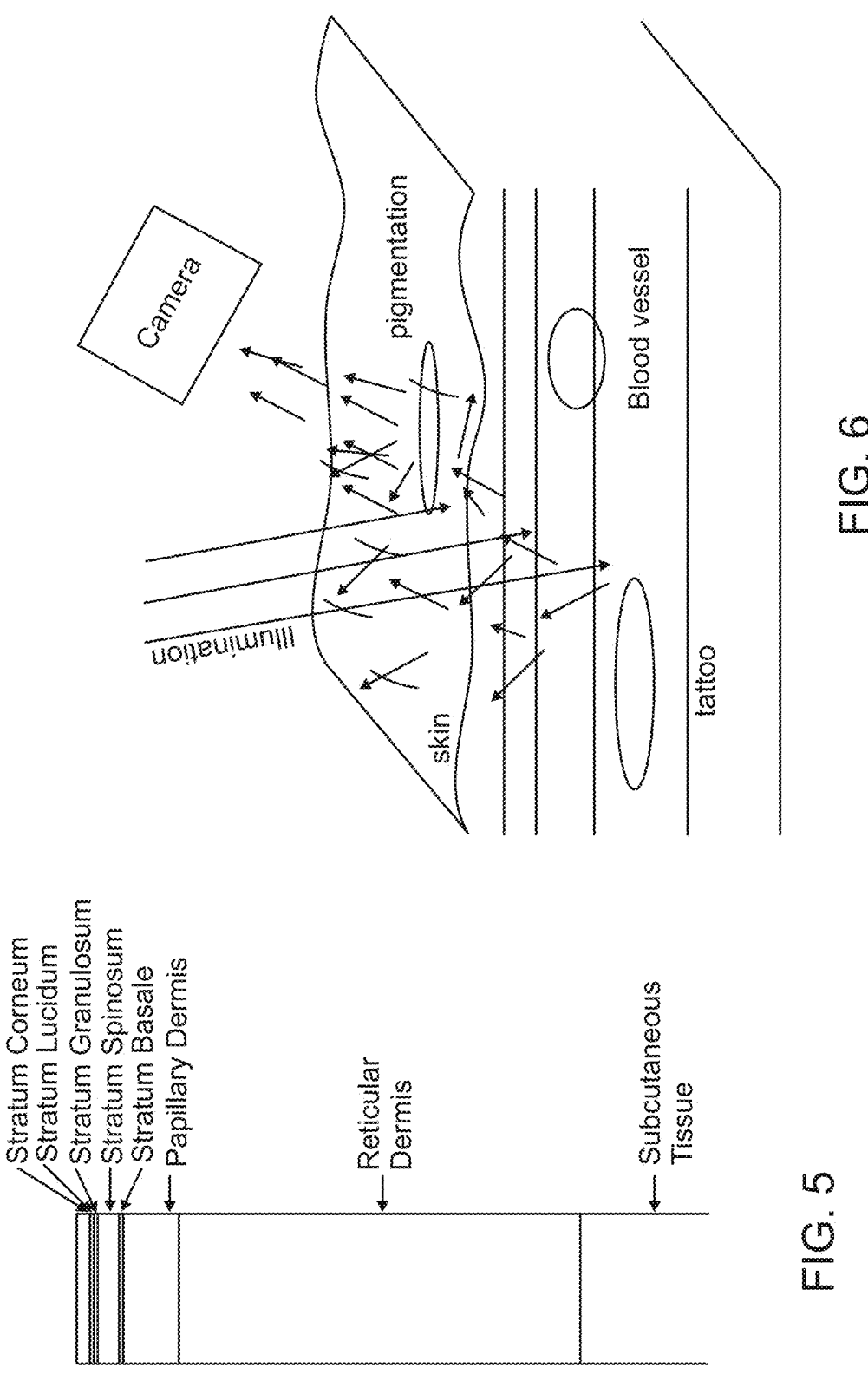
FIG. 5 illustrates the histological layers of typical human skin tissue.
FIG. 6 illustrates a schematic representation of light reflectance of various layers of human skin tissue.

Skin tissue is a very complex biological organ. Although the basic structure is common to all humans (see FIG. 5), there are many variations within the different areas in a specific individual and among individuals. Such variations include skin color (melanin content in Basal layer), hair color and thickness, collagen integrity, blood vessel structure, vascular and pigmented lesions of various types, foreign objects like tattoos, etc.

Figure 7:
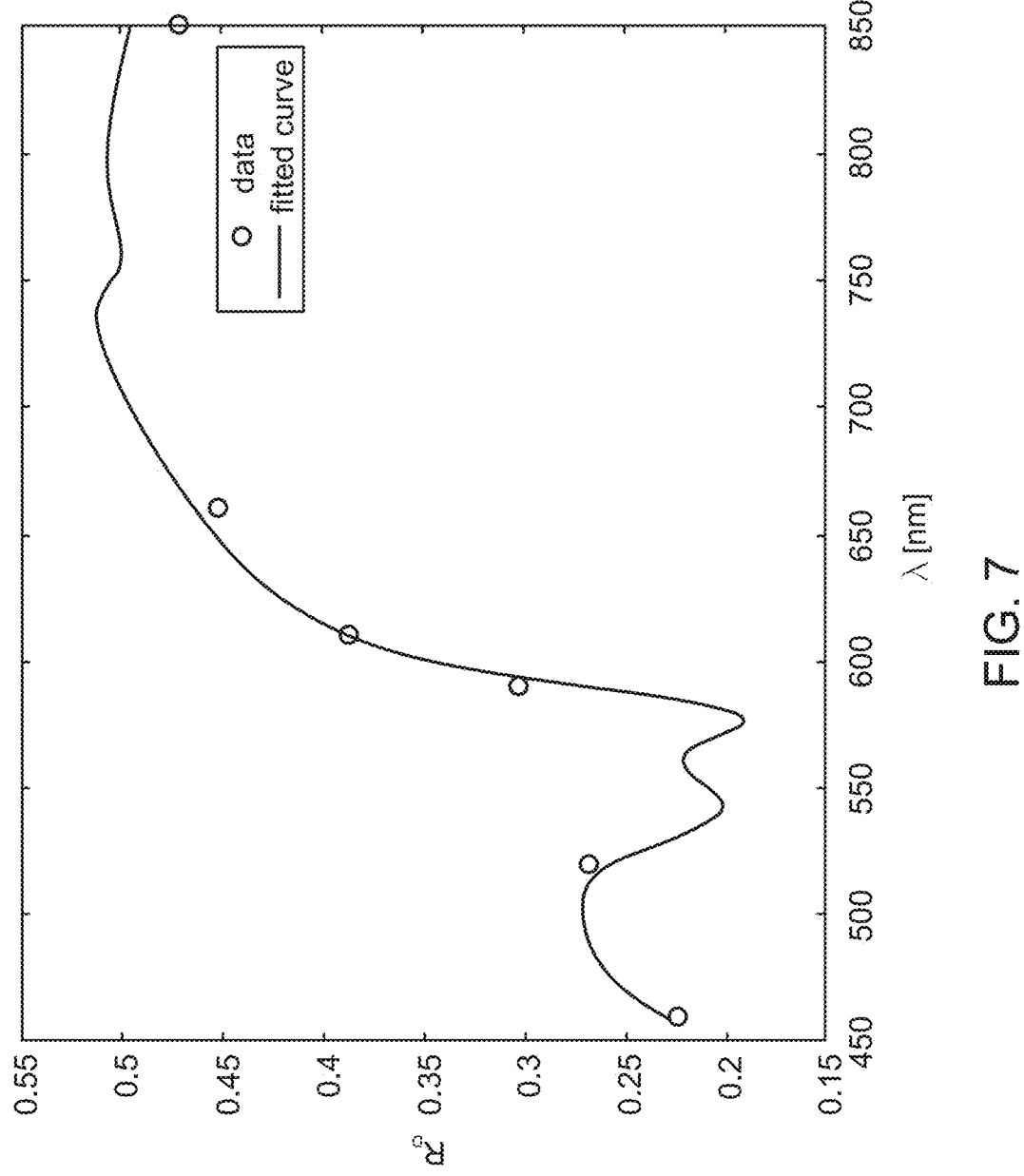
FIG. 7 illustrates a graphing of reflectance as a function of light wavelength for various skin color and blood types.

Integration of wavelength dependent scattering (FIG. 6) through tissue-layered structure determines the reflectance images that could be taken for various induced illuminations. Thus, reflectance imaging (different wavelengths, polarizations, and patterns) provides information about the basic skin optical and physical properties up to several millimeters in depth. FIG. 7 shows an example of the variation in total diffused reflectance spectra of a specific skin area with various levels of melanin, epidermal and dermal thickness and blood content and with respect to different light wavelengths. The circles on the graph represent 460 nm, 520 nm, 590 nm, 611 nm, 660 nm and 850 nm, the same wavelengths as used in the example of FIG. 9F, discussed below.

In the present application, a non-contact integrated treatment and imaging laser applicator will be described. It is designed to illuminate the treatment area with a series of different wavelengths, polarizations and spatial patterns and then to acquire a series of reflectance images prior to and immediately after the treatment. Using image processing, Principle Component Analysis (PCA), physical modelling and finally neural network algorithms, the obtained reflectance imaging data may be processed, and laser treatment parameters set. At a high level, this will be performed in three major phases: the pre-clinical and clinical data collection, algorithms training phase for classification and treatment prediction phase and algorithms validation phase.

Figure 8:
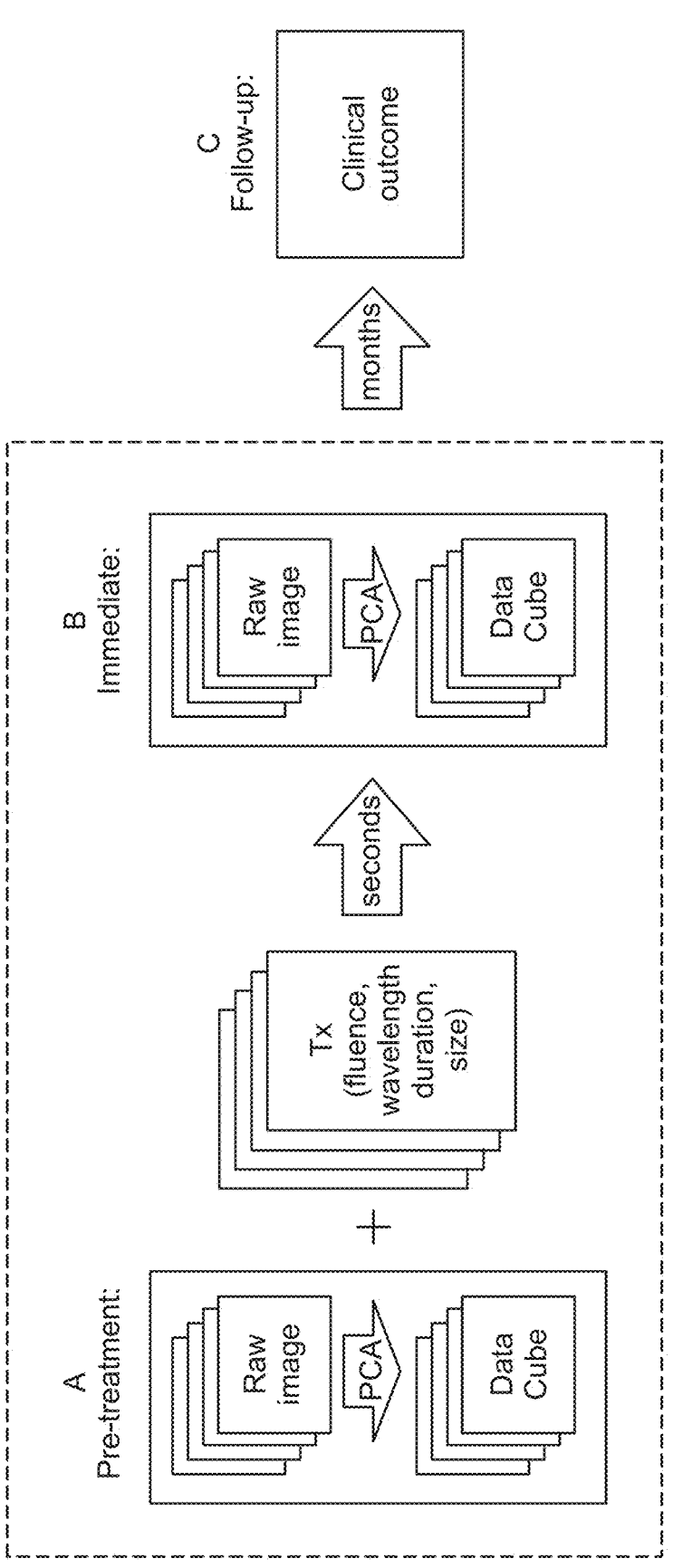
FIG. 8 illustrates a schematic high-level block diagram of data acquisition and processing within the present invention.

During the data collection phase, spectral images may be acquired dynamically in real time during the laser treatment, as schematically shown in FIG. 8. A pre-treatment multispectral image (A) will be followed by applying the laser treatment pulse (Tx) which can vary from nanoseconds duration for a tattoo and pigmented lesions removal treatment to tens of milliseconds for hair removal and vascular treatments. During the application of the treatment laser, the illumination and the imaging systems may be protected by providing a shutter. The treatment laser penetrates the skin tissue, gets absorbed by the chromophores and causes a cascade of reactions, including photochemical, thermal, acoustic and physiological. Those reactions create the desired treatment outcomes such as coagulation of soft tissue, mechanical breakdown of tattoo pigments followed by crusting, photo thermolysis, or vein collapse. Those immediate outcomes affect the absorption and scattering properties of the tissue and as such change the wavelength dependent reflection image. Those dynamic changes may be traced (B) as long as the target remains in the FOV of the imaging system.

The raw pre- and immediately post-treatment reflectance may be processed using Principal Component Analysis (PCA) which will enable robust classification of valuable parameters while reducing overall dimensionality of the acquired data. In other words, PCA differentiates data features with respect to their importance to the final clinical outcome (C). The most relevant parameters may be employed for the development of a physical laser-tissue interaction model, including, for example, thermal relaxation and soft tissue coagulation. Moreover, large amounts of highly correlated (A-Tx-B-C) data allow for construction of empirical equations which are based on quantitative immediate biological responses like erythema in hair removal and frosting formation in tattoo removal treatments. Currently, immediate responses are subjectively assessed in a non-quantitative manner by a trained physician without any dynamical quantification. Besides the commercial benefit, the platform envisioned by the present invention is a novel and robust research tool for clinical biological physics.

For most clinical indications, a user's guide of laser treatment parameters provided, usually by the manufacturer, is initially determined by various physical models and then verified by clinical experiments. As such, light-tissue interaction model is a valuable tool for gross clinical outcome prediction. The rule of thumb states that physical models may make 80% correct predictability in real life complex systems. The most effective way to boost the correctness of treatment parameters for desired outcomes may be by the use of artificial intelligence technology e.g. deep learning (DP). Deep learning involves the use of complex, multilevel "deep" neural networks to create systems that can perform feature detection from massive amounts of unlabeled training data and can easily outperform the old-fashioned physical reasoning approaches. An attempt to incorporate into a physical model all parameters and their sometimes multi factorial and weak correlations is tedious, complex, frequently impossible and most importantly can lead to instability of the solution.

In the long run, following an analysis in which clinical data will be collected, analyzed and correlated with the pre-treatment and short-term immediate post treatment spectral reflectance imaging data, a production version may be implemented in various laser treatment platforms. The product level system specifications will be relaxed as possible (per outcomes of this research program and user requirements). It may, by way of example, take a pre-treatment image (A) (FIG. 8) and, based on the huge prior collected database, decide on the best treatment parameters. It may also take a non-dynamical post-treatment image (B) to provide an initial feedback and assess the efficacy of the treatment based on the previously correlation clinical outcome database (C).

Figures 9A, 9B:
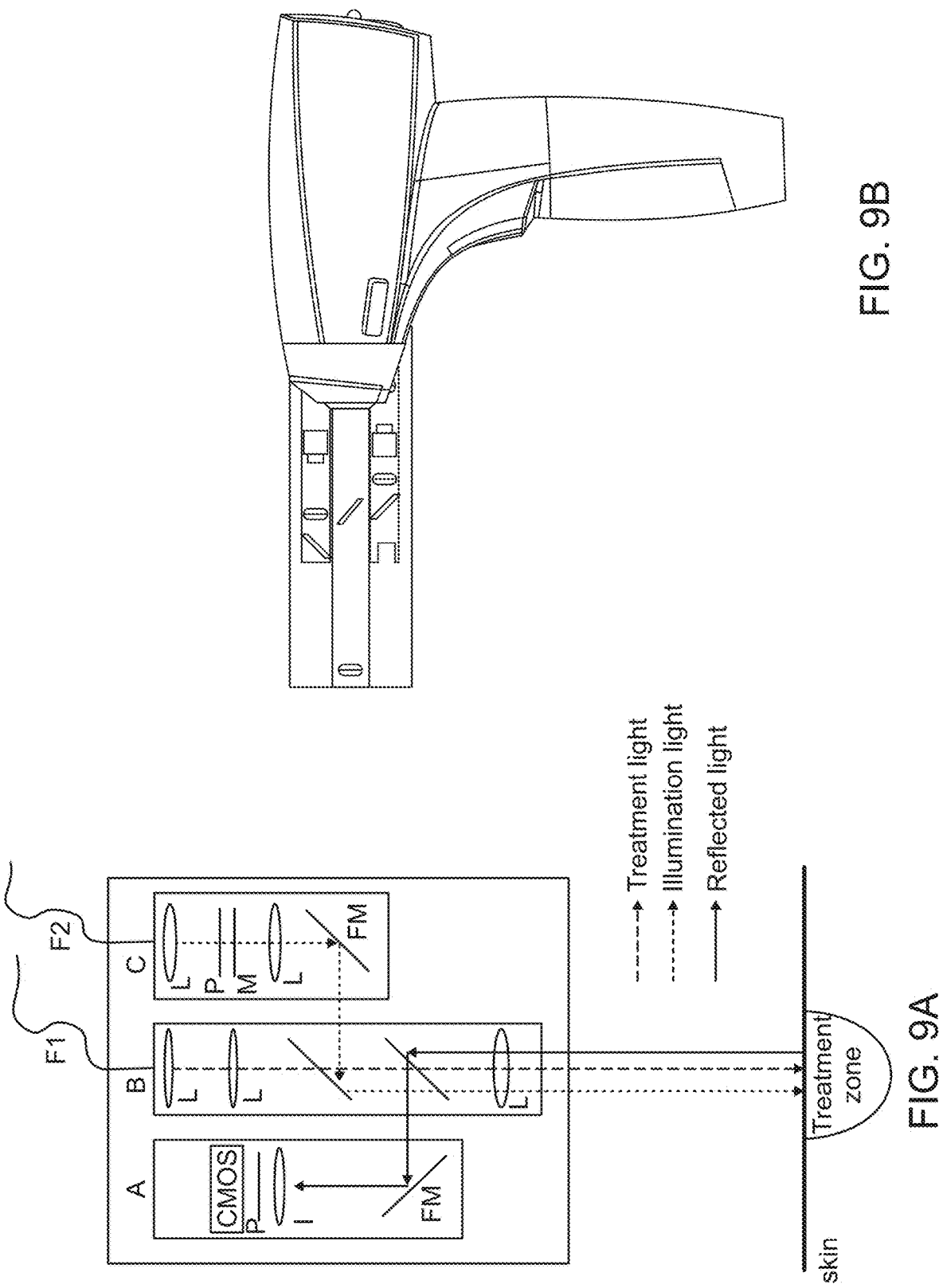
FIGS. 9A-9H illustrate schematics of various handpieces which embody aspects of the present invention.

One potential imaging treatment laser applicator is shown in FIG. 9A. It integrates three major components, which share the same output optics: the treatment laser portion, the illumination portion and the image acquisition portion. The requirements for the laser will vary with the clinical indication and affect the coupling into the applicator. Depending on the treatment, an articulated arm system, laser handpiece or a high-power fiber with a collimator may be attached to the back of a variable zoom system. The purpose of the zoom system will be to deliver a collimated treatment laser light to the desired target area of the target skin surface.

FIG. 9A includes: Portion A, an imaging portion including a zoom (L) and polarization optics (P), and a CMOS or other sensor(S). Further, the treatment laser portion B includes a high-power laser fiber (F1), zoom optics (L) and folding mirrors (FM). The illumination light portion C includes an illumination fiber (F2), zoom and polarization optics (P), optics (L) and Fourier spatial filtering (M). This is only an exemplary embodiment and many other variations may be implemented.

Within this portion of the applicator, a number (perhaps motorized) of folding mirrors may be mounted in order to switch between the illumination-imaging component and the treatment component. Adjacent to the treatment component is the illumination component portion C. Its purpose is to illuminate the target area with a series of wavelengths, polarizations and spatial patterns. It may include a light delivery fiber system with collimation optics, a polarizer, a variable special filter in the Fourier plane of illumination system and a folding mirror for the light to be able to propagate through the same path as the treatment laser. The wavelength of the illumination system can be controlled by applying an appropriate filter prior to the entrance to the illumination fiber. Finally, the third component of the applicator is an image acquisition and recording device A. It may consist of a CMOS/CCD sensor, a polarizer, variable wavelength filters, variable zoom optics and folding mirror to guide the light reflected from the skin surface, through the central applicator optics to the sensor.

In order to achieve the treatment device described above in regard to FIG. 9A, an adaptor for existing vendor products may be developed. For example, currently, for the assignor of the present invention, Lumenis Ltd, there are two handpieces on the market, first is M22 Multi-spot Nd:YAG which is used for veins, vascular lesions and hair-removal, and second is Q-switched Nd:YAG handpiece which is used for tattoo and pigmented lesions removal. Both handpieces have the same form factor and can be integrated as a treatment laser portion, as shown in FIG. 9B, into the imaging adaptor.

FIGS. 9C through 9G illustrate the adaptation of the present invention to other light-therapy devices.

Figure 9C:
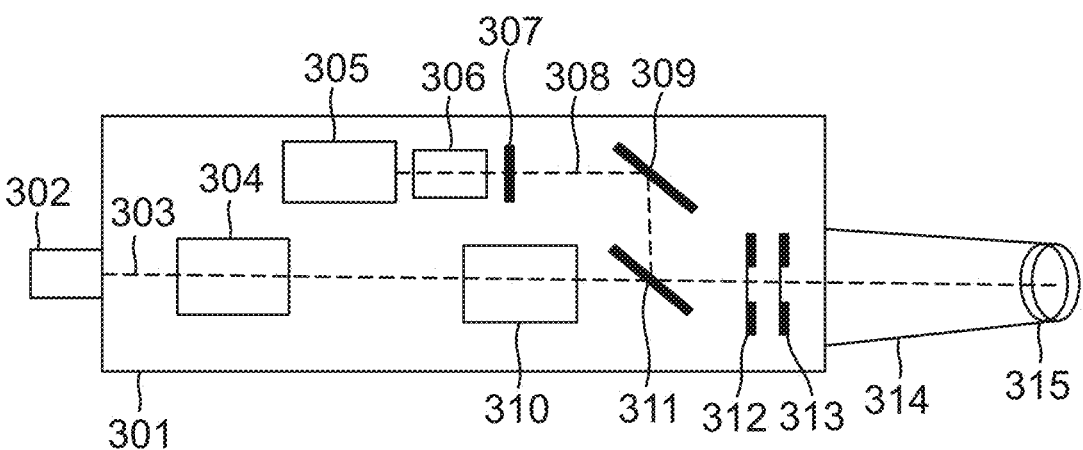

For example, FIG. 9C illustrates another embodiment suitable for a fiber-coupled laser source. In this embodiment, an applicator 301 is connected at 302 with a fiber laser source (not shown) of a known type. Within the applicator 301 is shown a laser beam axis path 303 emanating from the fiber laser source that traverses through the applicator and out the skin tip adaptor 314 as shown. The laser fiber optical axis 303 first travels through suitable laser collimating optical elements 304, then through laser focusing optics 310. A dichroic mirror 311 in next downstream along the optical axis 303. The laser beam then passes through an illumination ring 312 (to be described in detail in connection with FIG. 9F below) and then through a polarization optics ring 313. A calibration ring 315 is mounted at the distal end of the skin tip adaptor 314.

An illumination light source may be placed in line with the optical axis 303 to illuminate the skin tissue. When the illumination light source 312 is activated by a suitable programmable controller which may be contained within the console 10, light reflected from the skin tissue will be reflected back through the adaptor 314, rings 312 and 313 and then impinge on mirror 311. Mirror 311 deflects the reflected light to another mirror 309 along an imaging beam axis path 308 to polarization optics 307, focusing optics 306 and then to a CMOS/CCD sensor 305. The sensor 305 measures the light it receives and, in accordance with the present invention, analyzes the light and then may cause the modification of the output of the fiber laser source, all within suitable electronics and programming in the programmable controller. While an illumination ring light source 312 is shown and will be described below, it is to be understood that other suitable light sources may be provided in lieu of or in addition to ring 312.

Figure 9D:
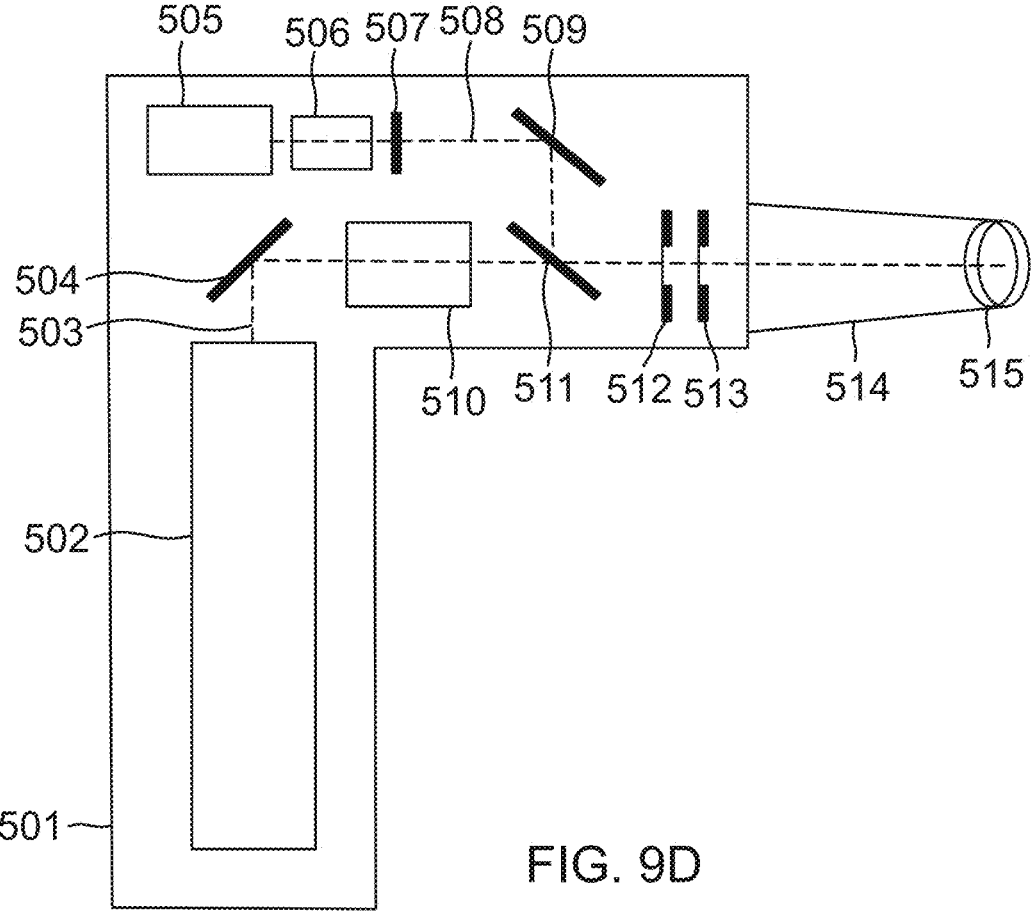

Turning now to FIG. 9D, this figure illustrates another combination laser/imaging device 501. Here, instead of a fiber laser input source, a laser module, which may be a solid-state laser source 502 of a known type, is included within the applicator. Otherwise, the optical paths and optical elements 503-515 correspond directly with such elements in the embodiment of FIG. 9C.

As with the embodiment of FIG. 9C, the embodiment of FIG. 9D also includes polarization optics ring 513 and illumination ring 512, the structure and function of each will be now discussed. The polarization optics ring 513 is provided to cross-polarize each of the images received from reflections from the skin tissue.

Figures 9E, 9F:
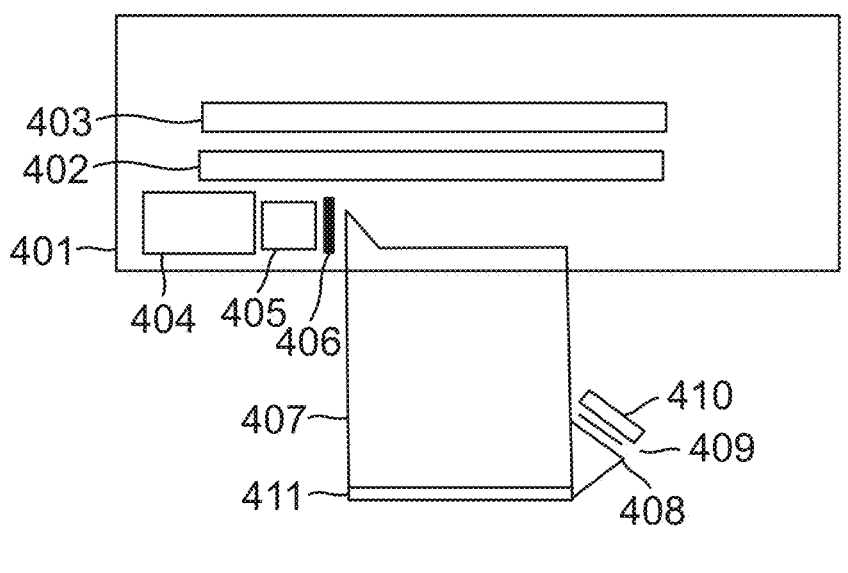
Figure 9G:
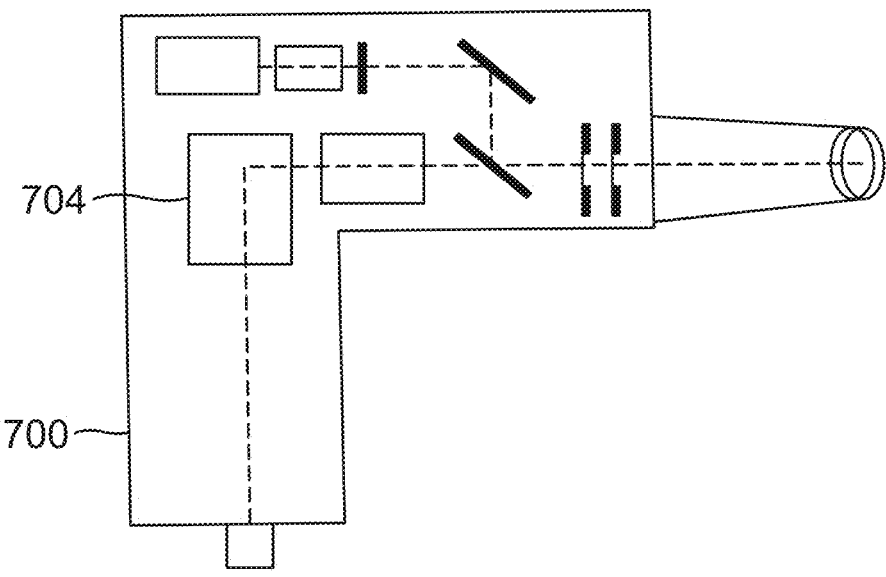
Figure 9H:
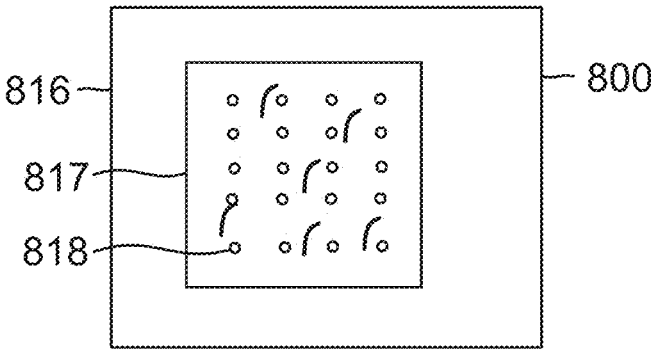

Turning now to FIG. 9G, that figure shows yet another embodiment of the present invention, in this case a fractional laser 700. The elements within the device of FIG. 9G are much the same as those in 9C and 9D, except with the addition of one or more known scanning mirrors 704 which direct laser energy to discrete separated spots on the skin tissue, as illustrated in FIG. 9H, wherein a display 800 on GUI 816 will, using the images from the CMOS/CCD sensor described above, display a live skin image 817 as well as the treatment spots 818.

Turning to FIG. 9F, this figure shows the illumination ring 512 in detail. Here, the ring may be a disk-like holder 600 with an opening 607 allowing for the passage of the laser beam therethrough as well as reflected light. Mounted around the periphery of the ring 600, a number of LEDs 601-606 are shown mounted. While the drawing only shows a certain number of LEDs, it is to be understood that any suitable number of LEDs (or other sources of light) and of varied wavelengths may be mounted on the ring 600.

By way of example only, the LEDs may be of wavelengths, generally in the range of 450 nm to 900 nm: 460 nm (601), 520 nm (602), 590 nm (603), 611 nm (604), 660 nm (605) and 850 nm (606). These wavelengths are, as mentioned, exemplary only and others may be used. The main goal is to provide a wide spectrum of illumination with which to apply to the skin, ranging from blue to red to IR, so that reflectance can be measured using sensors 305 or 505 described above. It is known that different wavelengths impinging on the skin tissue will have different depths of penetration and different reflectances/scattering. For example, while blue light may provide data concerning skin pigmentation at one end of the spectrum, red light may provide data at the vascular level and even deeper into the skin. By choosing and activating one or more of the LEDs, information/data as to the skin conditions can be sensed by the onboard sensors, for example, sensors 305 and 505. Data received by the sensors may be transmitted, through a suitable cable or wirelessly, to the console 10 and may be displayed on the user interface 12. A programmable controller within console 10 may read the output(s) of sensor 505, at one or more wavelengths, then process, through a suitable processor or computer unit, those outputs to determine what the settings for the laser unit 16 to apply to the tissue. The programmable controller may have a memory containing a lookup table that matches, for example, reflectance measurements to certain skin conditions, taking into account skin types, and control the application of laser treatment or provide the operator of the device with suggested treatment parameters or regimens. In addition, as such a device is used and readings from a number of patients are sensed and recorded, AI techniques may be used to further refine the treatment parameters and regimens.

Turning now to FIG. 9E, this figure illustrates the application of the present invention to an applicator that produces Intense Pulsed Light (IPL). IPL light sources are well-known per se in the art, but here the IPL source is modified in structure and operation.

The IPL applicator 401 includes an IPL lamp 403, and an IPL filter 402. Since the IPL lamp 403 is a source of incoherent light, the filter 402 is interposed between the lamp and the skin tissue to filter out unwanted wavelengths of light in a known manner. The applicator may include a lightguide 407 which may be placed in contact with the patient's skin tissue. The light guide may be of glass, sapphire or other (usually) transparent material. Light from the lamp 403 passes through the filter 402 and thence to and through the light guide 407. The filter 402 may be of the removable, replaceable type, such that, as with the light ring 600 discussed above, the target tissue may be impinged by different wavelengths of light.

Typically, light guides used in IPL devices may be rectangular in shape, but here are modified to include illumination coupling optics 408, polarization optics 409, an illumination plate 410 and calibration rim 411. The elements 408 through 410 function to illuminate the patient's skin tissue before, during and/or after treatment with the IPL light source, much as with the illumination systems described above in reference to FIGS. 9C and 9D.

Further, the lightguide 407 is further modified as seen in the upper left-hand corner in FIG. 9E to include elements 404, 405 and 406. These elements are a CMOS/CCD sensor 404, image focusing optics 405 and polarization optics 406. As with the previous embodiments, light illuminating the skin by way of illumination plate 410 is carried through the lightguide 407 to the sensor 404, and used as described above to perhaps modify the operation of the IPL light source.

1.2 Ultrafast Dynamic Scattering for Real Time Monitoring Based on Photodiodes Array The goal here is to provide a tool to monitor the treatment process on-line and provide feedback to the laser system to adjust treatment parameters and obtain efficacious treatment and reach the desired endpoint safely.

Monitoring the tissue condition before, during and after the treatment provides the clinician and the laser system the required information to make a decision on how to proceed. It is specifically advantageous to close the system loop and control various treatment parameters during the procedure. As in many cases the treatment period is short, a fast sensing and decision-making system that is capable of delivering feedback signals in a few milliseconds is preferable. A block diagram of the concept is presented in FIG. 10.

Figure 10:
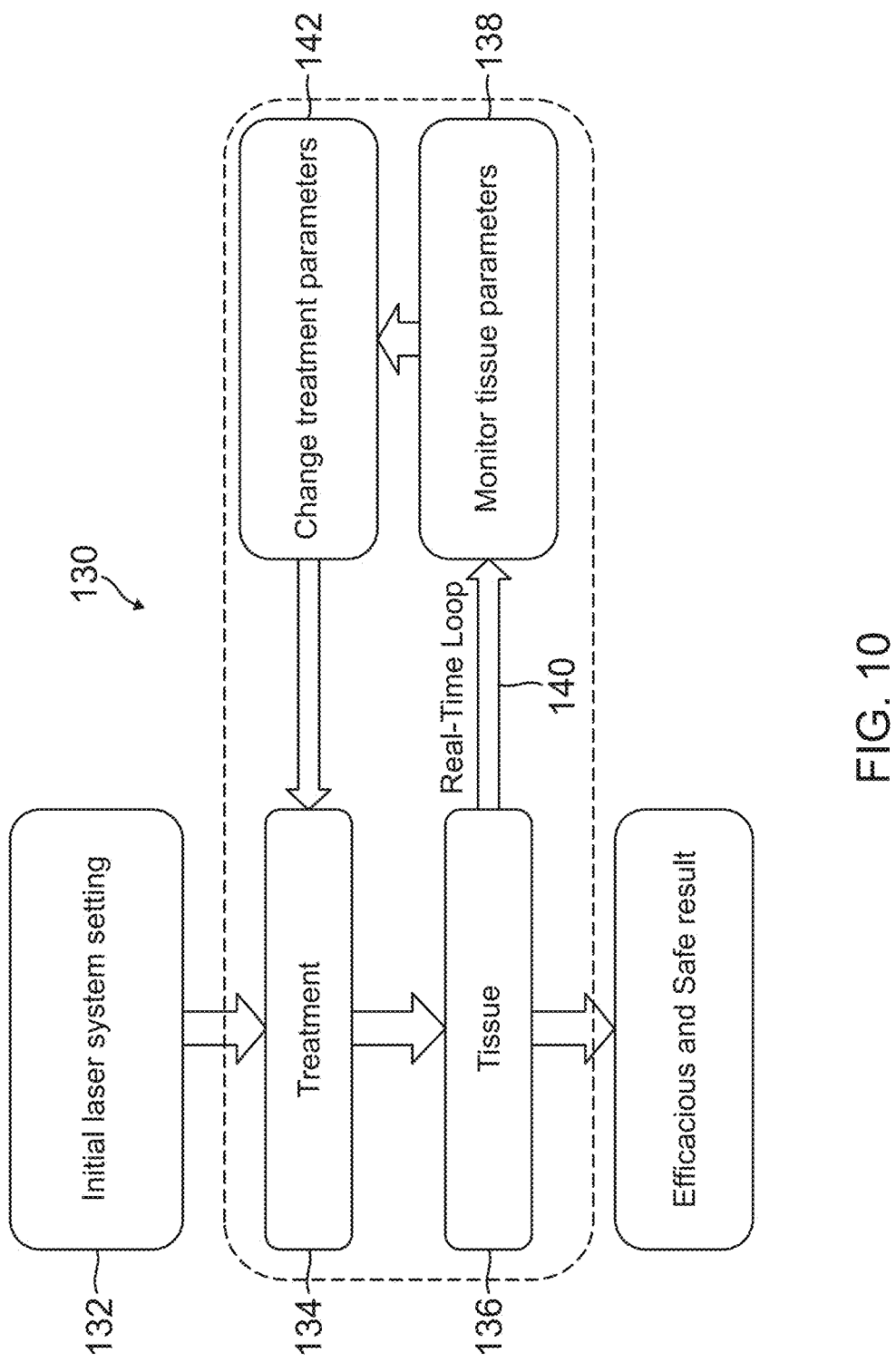
FIG. 10 illustrates the sequence of events concerning aspects of the present invention.

As shown in FIG. 10, the process of utilizing a system 130 includes the steps of: deciding on an initial laser system setting; applying treatment 134 to the tissue 136 using those settings; monitoring/examining/sensing the tissue treated 138; based on that monitoring/examination/sensing, in a real-time loop 140, changing the treatment parameters 142 as and if necessary or advisable.

Figure 11:
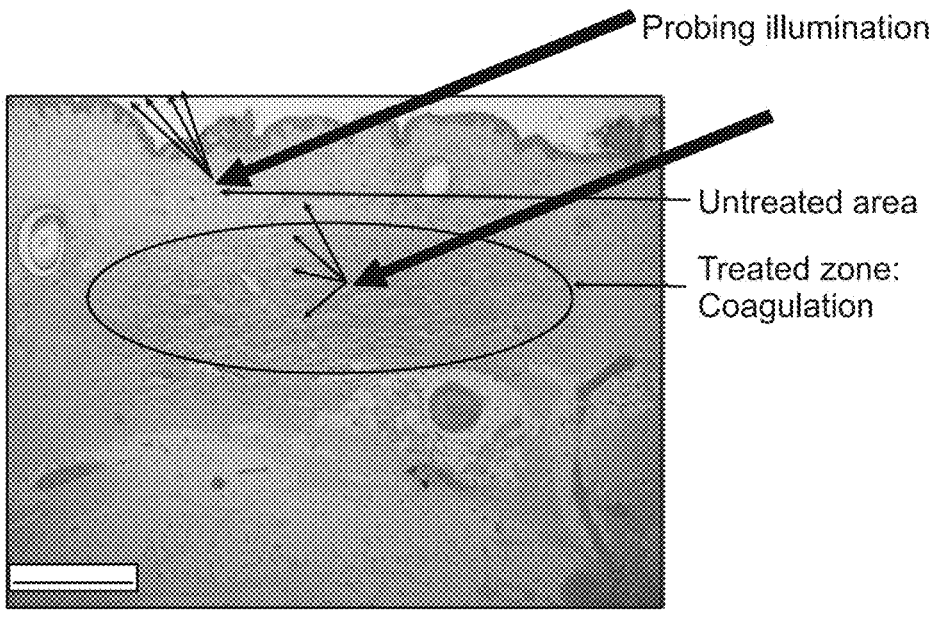
FIG. 11 illustrates scattering characteristics of light impinged upon skin tissue.

The proposed concept is based on monitoring optical tissue characteristics that tell something about the tissue condition e.g. normal tissue, coagulated tissue, melanin content. Two optical characteristics which may be considered may be absorption and scattering. The technique employed is to first illuminate the targeted tissue and then to measure the reflected light. Depending on temperature and treatment time, as tissue is treated and transformed into a new state, its inner structure is modified, and its absorption and scattering characteristics are altered (see FIG. 11). As there is a strong correlation between the scattering pattern and the skin condition, one can deduce information regarding this condition by monitoring the spatial distribution of the scattered light. To be able to use this information for applying real-time feedback to the laser system, this data acquisition and analysis preferably can provide this at or around 1 ms.

Figure 12:
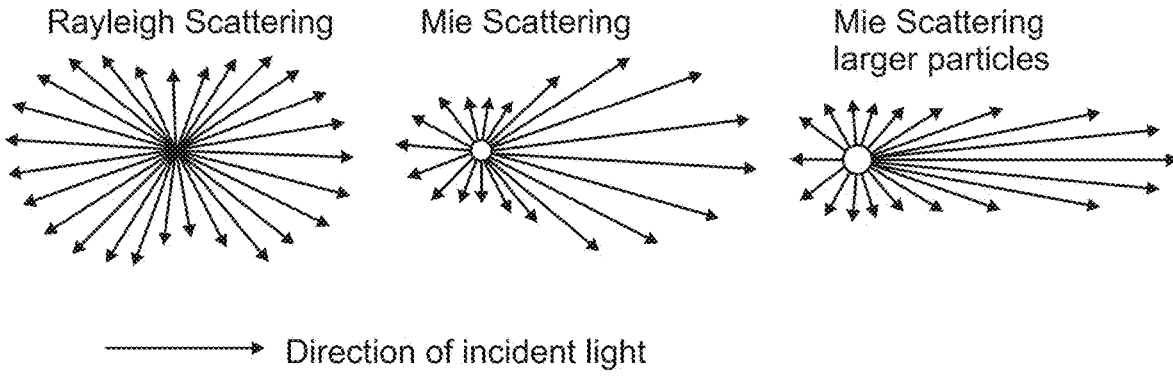
FIG. 12 illustrates the angular distribution of scattering characteristics of Mie and Rayleigh scattering.

When monitoring coagulation processes for example, the plan may be to monitor the scattering angular distribution as one moves from a Mie to a Rayleigh scattering pattern. This is shown schematically in FIG. 12. One can see that for scatters which are similar in size or larger than the wavelength (Mie scattering) most of the scattering is forward while for scatters smaller than the wavelength, as in the case of coagulated tissue, there is a shift into the Rayleigh regime, and the radiation is scattered to all directions. For other procedures, such as treating pigmented lesions, one might monitor the treated area absorption of light by monitoring intensity of the reflected light.

Figure 13:
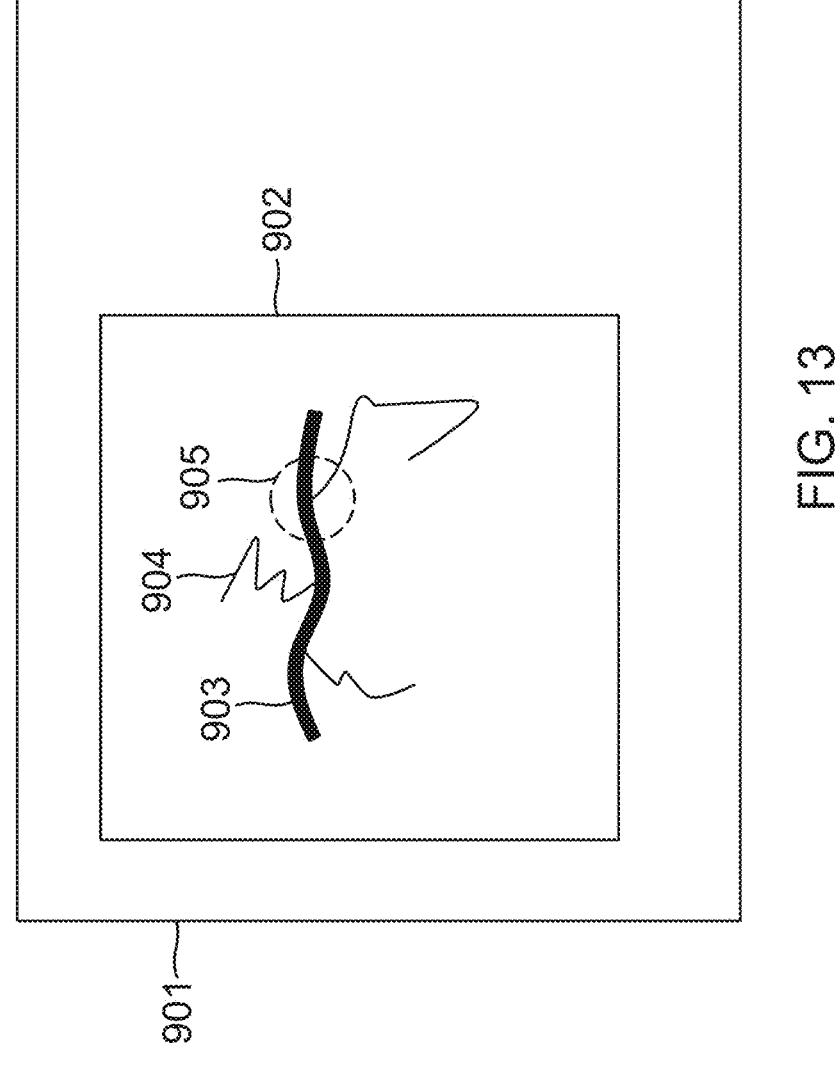
FIG. 13 illustrates an image of a display on a GUI or other device during a procedure.

FIG. 13 illustrates a representation of a display screen or GUI 901 on a console just prior to, during and after the treatment procedure. As discussed above, prior to activating the treatment laser device, a live skin image 902 of the area of treatment may be displayed on the GUI 901. By varying the wavelength of the light sources of FIG. 9F discussed above and herein, various tissue depths may be probed and displayed. In the example of FIG. 13, superficial veins 904 and deeply located "feeder" veins 203 may be displayed at 905. The operator of the device can then decide what type of treatment is desired and activate the laser device which may provide treatment based on a protocol stored within the device. However, with the present invention as described herein, the device may be programmed to image the skin tissue, as in FIG. 13, and then more or less autonomously, based on the images, activate a treatment protocol to the patient's skin tissue.

Figure 14:
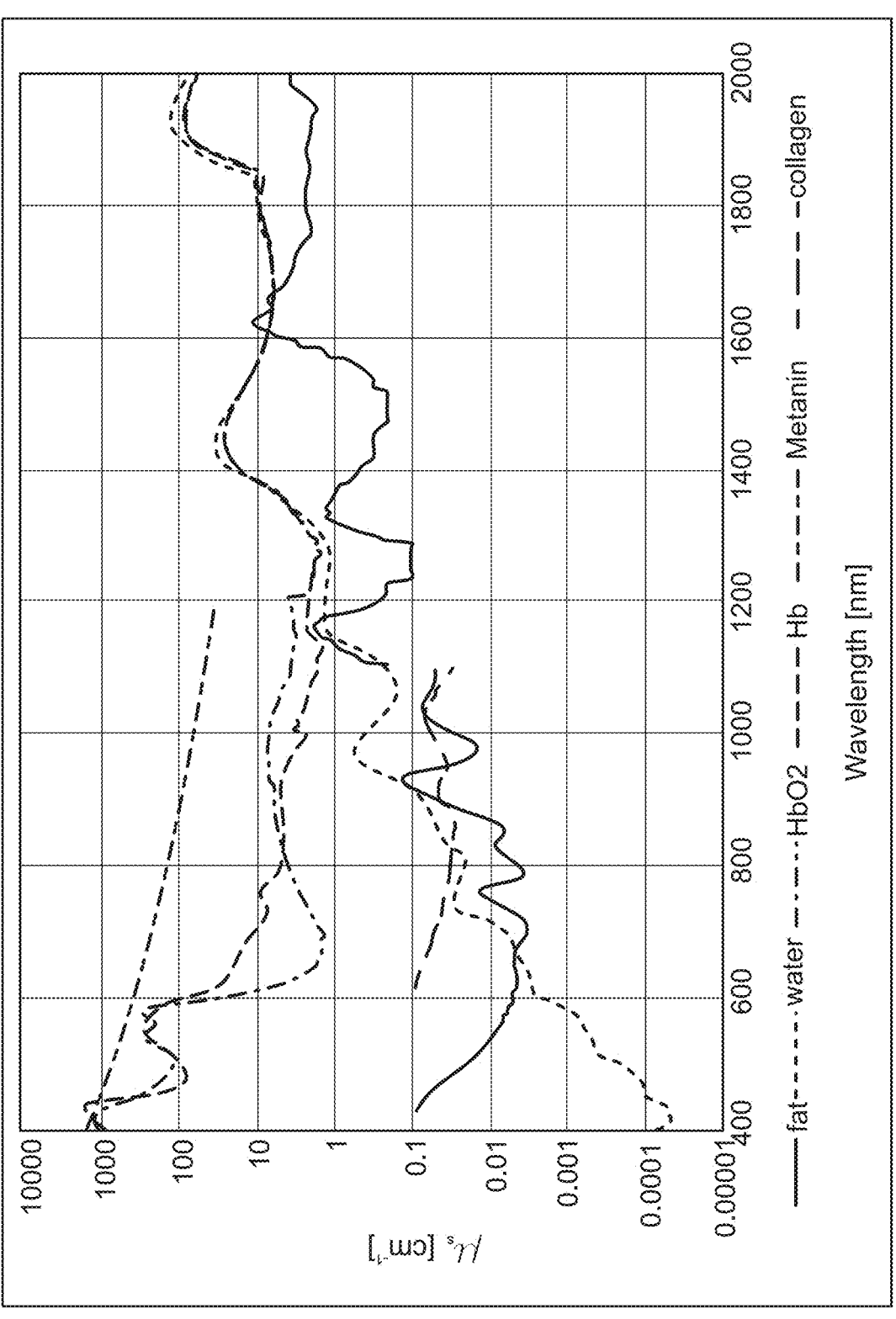
FIG. 14 illustrates spectra of various chromophores.

The characteristic spectral scattering of skin tissue and absorption coefficients for selected chromophores is presented in FIG. 14.

Figure 15:
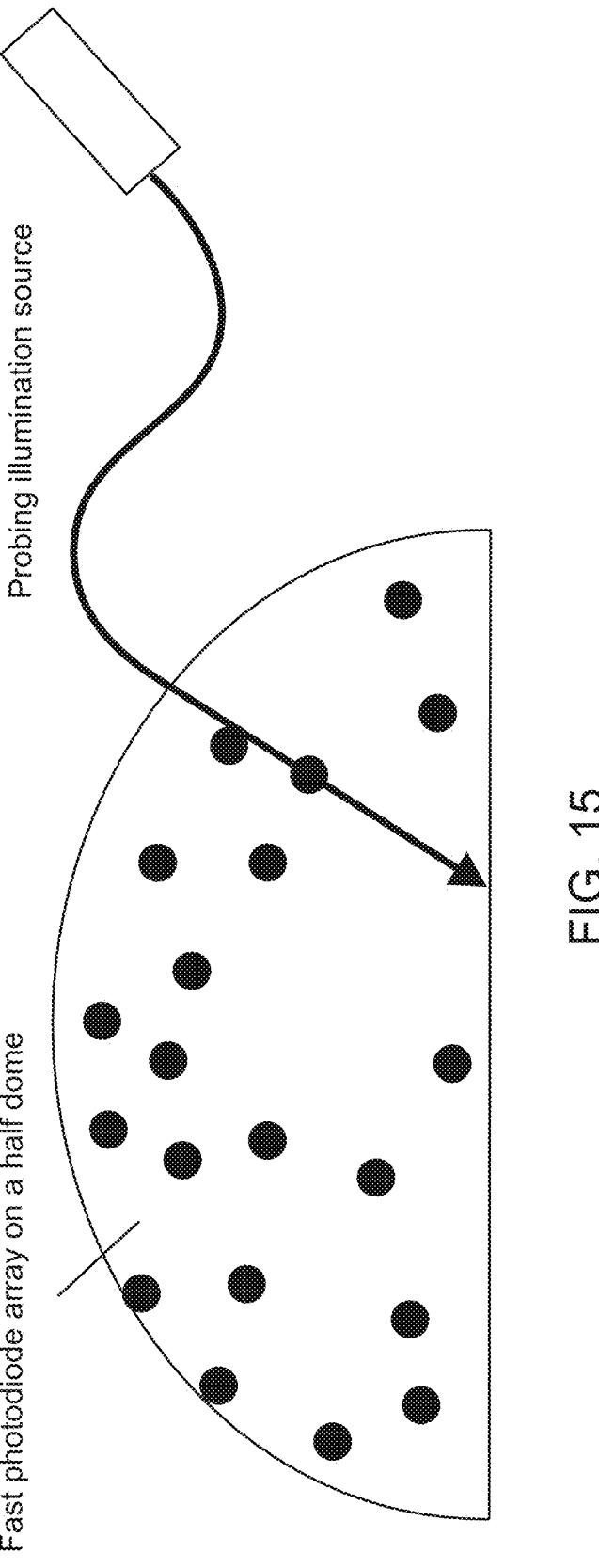
FIG. 15 illustrates one embodiment of a skin monitoring device.

One implementation of a monitoring device may be done by using a fast photodiodes array, arranged in a half dome configuration (as shown in FIG. 15). By using different wavelengths to monitor different depths and different aspects of conditions of the tissue, more information can be garnered to enhance the decision-making algorithm. In this way, one can monitor the spatial distribution of the scattered light, assess the tissue condition and deduce the preferred laser settings.

Few simultaneous probing channels may fit several applications. For example, one can use target and reference channels to monitor the treatment process and bring the optical end point to a unique and personal level. In another application, Real Time Spatial Frequency Domain Slicing, one can use light sources that generate different spot sizes or different spatial patterns. As the spatial frequency decreases (spot size increases) light penetration depth increases, and information may be obtained of deeper levels in the tissue. Thus, by subtracting the data obtained from several cumulative depths, one can obtain information which comes from a specific layer inside the tissue.

Figure 16:
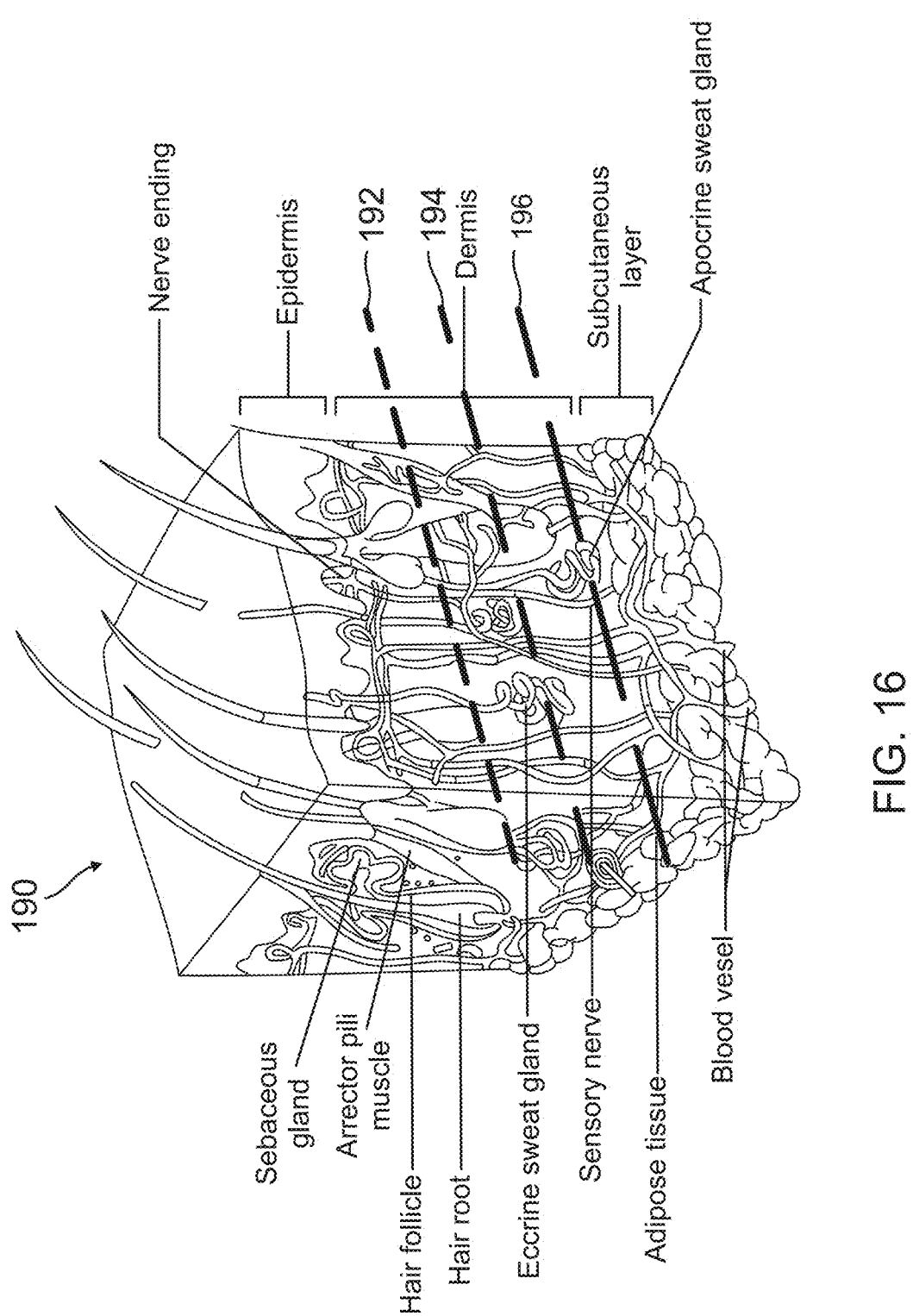
FIG. 16 illustrates the results of ascertaining information from skin tissue as a result of using spatial frequency domain slicing.

As may be seen in FIG. 16, showing a cross-sectional view of skin tissue 190, one type of illumination of the target with one spatial modulation may generate information of that skin from one depth 192, while use of another spatial modulation may reveal information at a deeper depth 196. By measurement of the scattering and intensity of both data sets, one can use lock-in detection with two different frequencies for each of them. The difference in data can be used to extract real time information which is specific for the layer 194 between layers 192 and 196. If desired, one can generate further illumination patterns to discern additional skin tissue layers.

Another implementation of using multi-channels of illumination is for spectral real-time monitoring. By that, more data is added to the feedback function to make decisions more accurate. This is particularly important when trying to determine safety end points. This is true not only for laser treatments based on thermal processes such as coagulation but also in photo-acoustic based treatments such as tattoo removal where repetitive illumination on the same or adjacent spot is common. By smart real-time data analysis, skin conditions can be monitored, with the additional ability to stop the treatment in case of detected changes that might lead to adverse events.

Yet another implementation of this technology may be by using it to create a real-time spectral image of the focal treatment area. This may be done by mimicking the concept of the compound eye possessed by insects. The compound eyes (see FIG. 17) consist of thousands of ommatidia, which are tiny independent photoreception units that consist of a cornea, lens, and photoreceptor cells which distinguish brightness and color. In nature, images perceived by, for example, an insect are a combination of inputs from the numerous ommatidia, which are oriented to point in slightly different directions. Compared with single-aperture eyes, compound eyes have poor image resolution; however, they possess a very large view angle and possess the ability to detect fast movement and, in some cases, the polarization of light.

Figures 17, 18, 19:
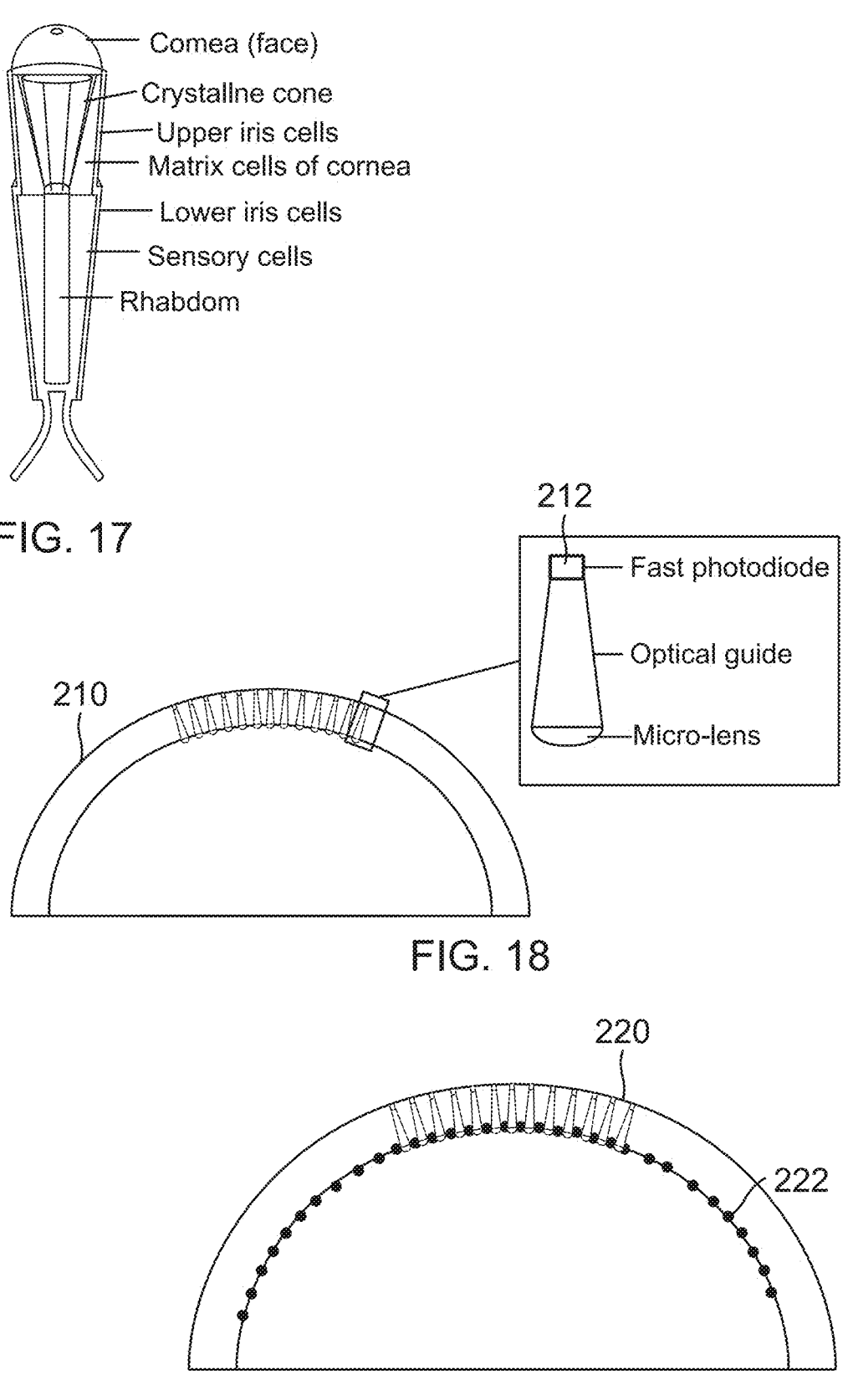
FIG. 17 illustrates one embodiment of the structure of an ommatidium used with the present invention.
FIG. 18 illustrates a half-dome structure with ommatidia implanted in the shell of the structure.
FIG. 19 illustrates another half-dome structure like FIG. 18 but with added wide-angles sensors mounted on the inner surface of the structure.

By embedding sensors 212 in an artificial manmade ommatidium-like structure embedded in the half dome structure 210 of FIG. 18 ensuring that the different "ommatidia" have different FOV and that together they cover the entire ROI, an image of the ROI may be obtained. Since the sensors are fast and can have simultaneous spectral signal pickup (illumination dependent), a fast-spectral imaging device can be obtained. To allow easier and denser assembling, one can use fiber coupled sensors, so on the dome there are only fiber ports.

By using different optical designs of the "ommatidia", overlapping of their FOV can be generated or avoided. There are advantages and drawback for each of those approaches and the final design will strongly depend on the real-time feedback logic that will be implemented.

By combining in a half dome array of fast photodiodes, such as is shown in FIG. 19, both types of optical designs i.e. cluster of narrow fields of view photodiodes 220 directed to the focal area of treatment, and array wide field of view photodiodes 222 one can attain both types of information: focal spectral image from actual treatment spot and spectral scattering distribution.

Figure 20:
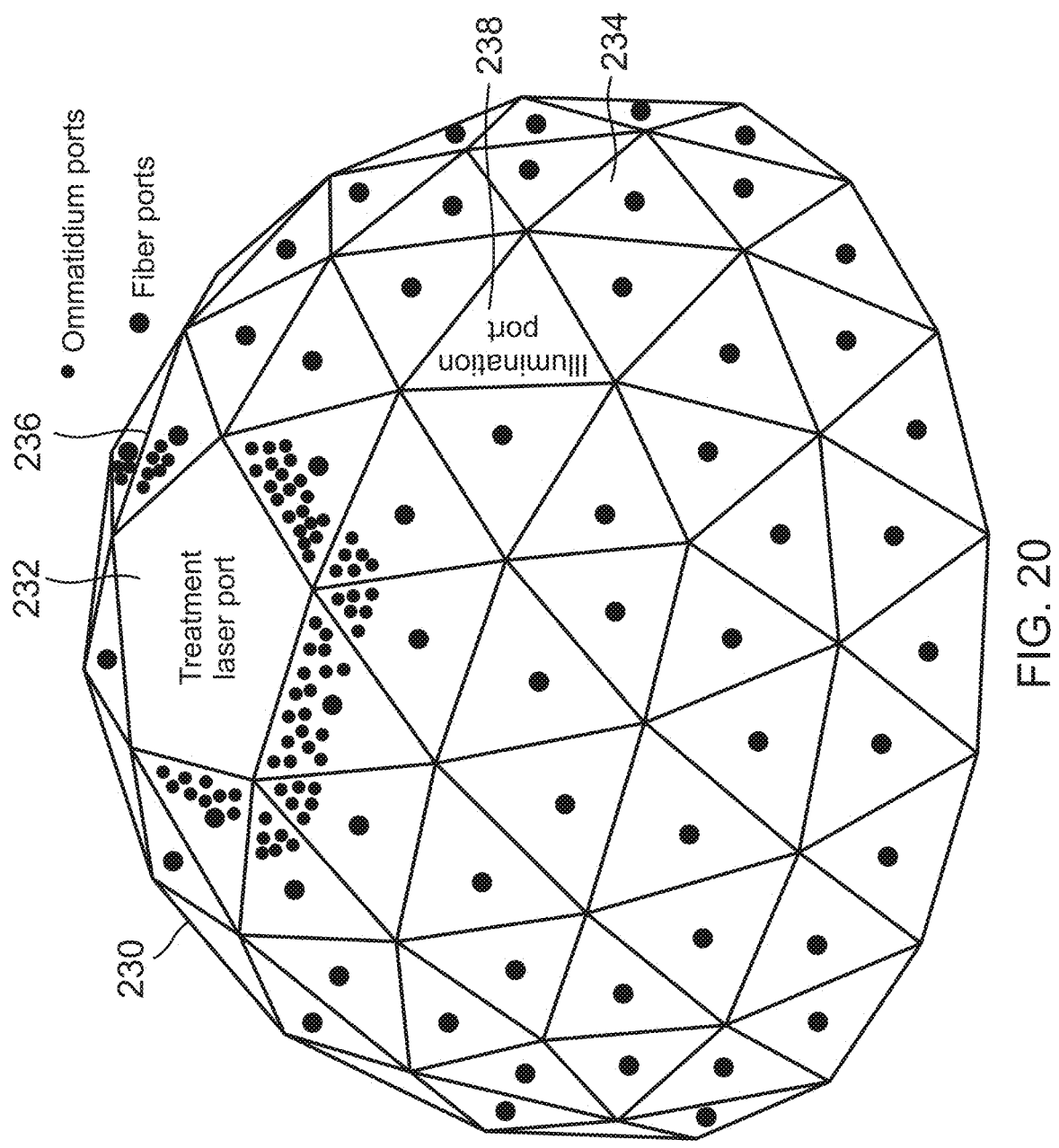
FIG. 20 illustrates a dome structure with a treatment laser port, an illumination port, fiber ports for fast photosensors, and ommatidium ports.

An initial possible implementation, as shown in FIG. 20, includes fast photodiodes with fast electronics as the basic building block. With current technology one can achieve sampling rates as high as few GHz, more than enough for this application. The spatial distribution acquisition can be solved by building an array of said sensors in a form that captures the 3D angular distribution of the scattered light i.e. a half dome pattern. To allow packed tiling of these sensors, fiber coupled sensors can be used. The half dome configuration of FIG. 20 consists of a geodesic-type dome 230 with the surface elements used as bases for various functional ports: treatment laser port 232, fiber ports for the fast photo-sensors 234, ommatidium ports 236 and one or more illumination ports 238 which can also be fiber coupled. The array of sensor elements may be based on off-the-shelf components, such as Thorlabs DET025AFC Fiber-Coupled Si Detector (2 GHz bandwidth, 150 ps rise time 400 nm-1100 nm). To achieve good signal to noise ratio and enable multi-channel analysis, lock-in detection may be incorporated and modulate the probing light source. For simultaneous multi-channel analysis, several probing light sources may be used, each with different modulation frequency. A simple lock-in amplifier per sensor per channel could be implemented using, for example, Analog-Devices AD630 Balanced Modulator/Demodulator.

These sensors may be used for imaging, using the compound eye concept described above. Some or all of the fiber ports may be engineered in a way that creates an artificial ommatidium. Clusters of such ports on the same geo-dome surface element may be used and implemented on selected elements to ensure that the required field of view is obtained.

Figure 21:
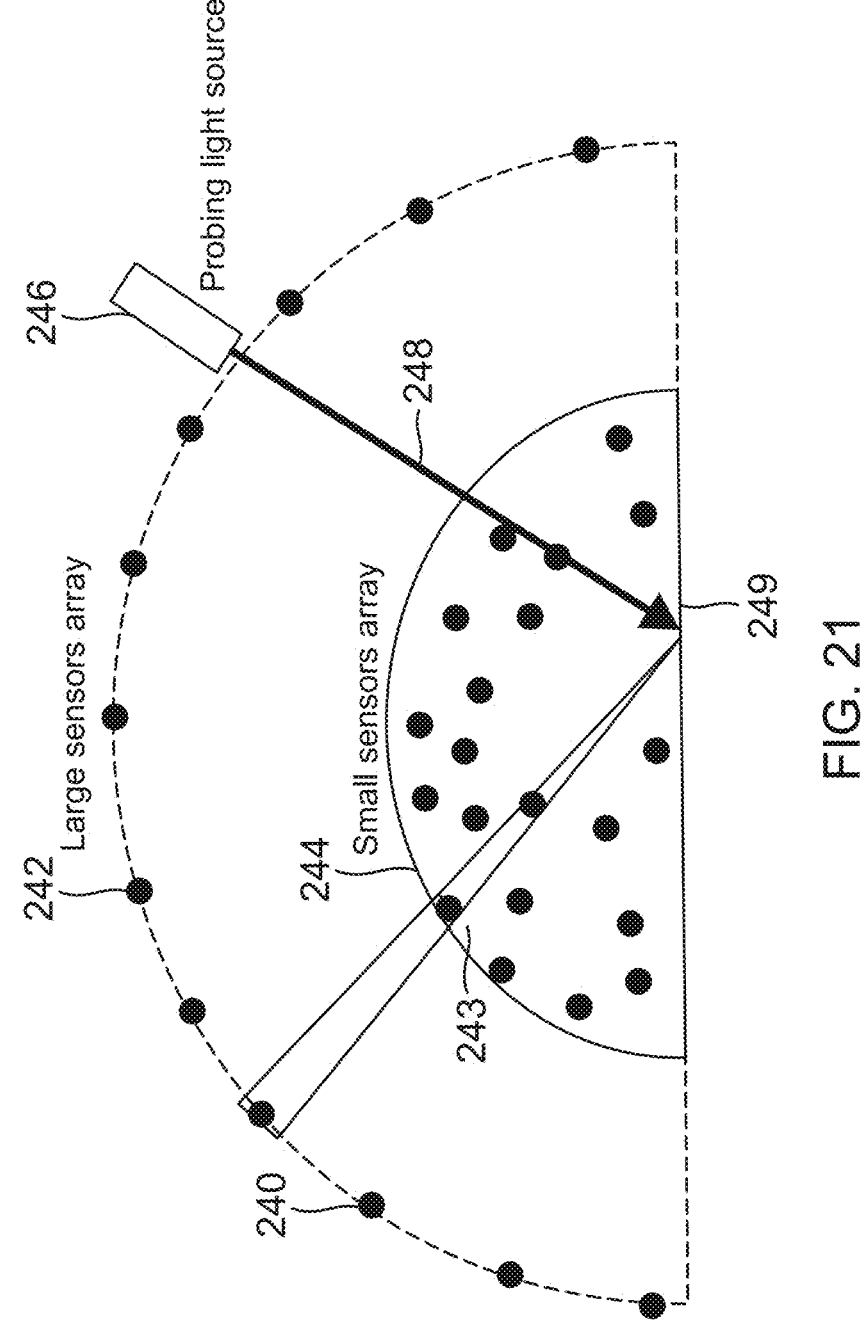
FIG. 21 illustrates another embodiment of a half-dome structure with mounted sensors.

Another dome arrangement is shown in FIG. 21. FIG. 21 shows a dome structure 240 with a large sensor array 242 and a small sensor array 244, a probe light source 246 that projects a beam of light 248 that is reflected 243 at skin surface to sensors in both the small array and the large array.

The proposed technology may well provide significant benefits over present commercial devices because none appear to propose real-time monitoring of tissue characteristics at acquisition rates which enable real-time feedback to the treatment process itself.

The skin diagnosis technology described herein may serve as a platform for the development of next generation medical laser products and new laser module technologies. Having a technology that measures in real time the skin and target lesion properties may drive in the future efforts to develop multi-wavelength laser technology that can switch wavelengths (and other laser attributes) in real time accordingly. Moreover, the skin diagnostic technology may be extended to support and enhance clinical diagnosis of the lesions. For example, it may be able to differentiate between benign vs. cancerous pigmented lesions. This may have major effect on patient management decisions. Moreover, the skin diagnostic technology developed may serve as a novel and powerful research tool, for the development of new applications and lasers.

What we claim is:

1. A cosmetic method of treating skin tissue with a source of treatment light comprising:

providing a handpiece comprising:

a source of treatment light that provides, when activated, a light path for treatment light to impinge upon the skin tissue along an optical axis;

the optical axis being defined by a propagation path of the treatment light after activation of the source of treatment light;

one or more sources of illumination light that provide, when activated, illumination light towards the skin tissue to generate an illumination light path along the optical axis, wherein the one or more sources of illumination light direct the illumination light from the one or more sources of illumination light to impinge on the skin tissue along the optical axis, the one or more sources of illumination light comprising one or more illumination LED light sources;

one or more sensors positioned along a second optical axis parallel to the optical axis and configured to measure, when activated, illumination light reflected from the skin tissue resulting from the illumination light, along or the illumination light path;

providing a programmable controller;

activating, by the programmable controller, the one or more of the illumination LED light sources, the one or more illumination LED light sources directing the illumination light to the skin tissue along the optical axis, the illumination light from the one or more illumination LED light sources being reflected from the skin tissue along the optical axis and then to the second optical axis to the one or more sensors;

enabling, by the programmable controller, the one or more sensors to measure the illumination light reflected from the skin tissue;

receiving, by the programmable controller, information sensed of measured reflected illumination light from an output of the one or more sensors;

processing, by the programmable controller, the information sensed of measured reflected illumination light to determine conditions of the skin tissue;

determining, by the programmable controller, a treatment light regimen based on the determined conditions of the skin tissue; and activating, by the programmable controller, the source of treatment light according to the treatment light regimen to provide treatment light along the treatment light path to impinge the skin tissue and treat the skin tissue according to the treatment light regimen.

2. The method of claim 1, further comprising the step of providing light directing elements to direct both the source of treatment light and the one or more illumination LED light sources along or parallel to the optical axis.

3. The method of claim 1, further comprising the step of selecting, by the programmable controller, one or more wavelengths from the one or more illumination LED light sources having different wavelengths and activating the one or more illumination LED light sources to illuminate the skin tissue at the one or more wavelengths.

4. The method of claim 1, wherein the treatment light source is selected from one or more of: a fiber laser source, a solid-state laser source, an Intense Pulse Light (IPL) light source, and a LED light source.

5. The method of claim 1, wherein the skin tissue is treated for one or more categories of: pigmented lesions, vascular removal, tattoo removal, and hair removal.

6. The method of claim 5, further comprising the step of selectively activating, by the programmable controller, one or more of the one or more illumination LED light sources dependent upon a category of skin tissue treatment.

7. The method of claim 1, further comprising the step of activating, by the programmable controller, one or more of the one or more illumination LED light sources dependent on the desired depth of light penetration into the skin tissue.

8. The method of claim 1, further comprising the step of:

reactivating, by the programmable controller, after the step of treating the skin tissue, the one or more illumination LED light sources to produce illumination light directed to the skin tissue;

reenabling, by the programmable controller, the one or more sensors to measure the illumination light reflected from the skin tissue;

receiving, by the programmable controller, from the output of the one or more sensors, second information sensed of the measured reflected light;

processing, by the programmable controller, the second information sensed to determine second conditions of the skin tissue after treating the skin tissue; and generating, by the programmable controller, a second treatment light regimen based on the second conditions of the skin tissue.

9. The method of claim 1, wherein the step of the programmable controller processing the measured light received from the output of the one or more sensors and providing a treatment light regimen includes the step of analyzing, by the programmable controller, the measured light received and matching it to memory information contained in a lookup table in a memory associated with the programmable controller, and selecting the treatment light regimen based on a match in the lookup table.

10. The method of claim 1, wherein the step of the programmable controller processing the measured light received from the output of the one or more sensors and providing a treatment light regimen includes the step of the programmable controller being configured to analyze the measured light received and match it to information contained in a memory associated with the programmable controller, and selecting the treatment light regimen based on a match.

11. The method of claim 1, wherein the step of the programmable controller processing the measured light received from the output of the one or more sensors and providing a treatment light regimen includes the step, by the programmable controller, of matching the measured light received to memory information using artificial intelligence methods and deep learning contained in a memory associated with the programmable controller, and selecting the treatment light regimen based on a match.

12. Apparatus for treating skin tissue with a source of treatment light comprising:

a handpiece comprising:

a source of treatment light that provides, when activated, a light path for treatment light to impinge upon the skin tissue along an optical axis;

the optical axis being defined by a propagation path of the treatment light after activation of the source of treatment light;

one or more sources of illumination light that provide, when activated, illumination light towards the skin tissue to generate an illumination light path along the optical axis, wherein the one or more sources of illumination light direct the illumination light from the one or more sources of illumination light to impinge on the skin tissue along the optical axis, the one or more sources of illumination light comprising one or more illumination LED light sources;

one or more sensors positioned along a second optical axis parallel to the optical axis and configured to measure, when activated, illumination light reflected from the skin tissue resulting from the illumination light along the illumination light path;

a programmable controller, the programmable controller, configured to:

activate the one or more of the LED illumination light sources to direct the illumination light to the skin tissue, the illumination light from the one or more illumination LED light sources being reflected from the skin tissue along the optical axis and then to the second optical axis to the one or more sensors;

enable the one or more sensors to measure the illumination light reflected from the skin tissue;

receive information sensed of measured reflected illumination light from an output of the one or more sensors;

process the information sensed of measured reflected illumination light received to determine conditions of the skin tissue;

determine, a treatment light regimen based on the determined conditions of the skin tissue; and activate the source of treatment light according to the treatment light regimen to provide treatment light along the treatment light path to impinge the skin tissue and treat the skin tissue according to the treatment light regimen.

13. The apparatus of claim 12, further comprising light directing elements to direct both the source of treatment light and the one or more illumination LED light sources along or parallel to the optical axis.

14. The apparatus of claim 12, wherein the programmable controller is configured to select one or more wavelengths from the one or more illumination LED light sources having different wavelengths and activate the one or more illumination LED light sources to illuminate the skin tissue.

15. The apparatus of claim 12, wherein the treatment light source is selected from one or more of: a fiber laser source, a solid-state laser source, an Intense Pulse Light (IPL) light source, and a LED light source.

16. The apparatus of claim 12, wherein the skin tissue is treated for one or more categories of: pigmented lesions, vascular removal, tattoo removal, and hair removal.

17. The apparatus of claim 16, further comprising the programmable controller being configured to selectively activate one or more of the one or more illumination LED light sources dependent upon a category of skin tissue treatment.

18. The apparatus of claim 12, further comprising the programmable controller being configured to activate one or more of the one or more illumination LED light sources dependent on the desired depth of penetration into the skin tissue.

19. The apparatus of claim 12, further comprising the programmable controller being configured to:

reactivate, after the step of treating the skin tissue, the one or more illumination LED light sources to produce illumination light directed to the skin tissue;

reenable, the one or more sensors to measure the illumination light reflected from the skin tissue;

receive, from the output of the one or more sensors, second information sensed of the measured reflected light;

process the second information sensed to determine second conditions of the skin tissue after treating the skin tissue; and generate a second treatment light regimen based on the second conditions of the skin tissue.

20. The apparatus of claim 12, wherein the programmable controller is configured to process the measured light received from the output of the one or more sensors and provide a treatment light regimen by analyzing the measured light received and matching it to memory information contained in a lookup table in a memory associated with the programmable controller, and selecting the treatment light regimen based on a match in the lookup table.

21. The apparatus of claim 12, wherein the programmable controller is configured to process and analyze the measured light received from the output of the one or more sensors by matching the measured light received to memory information contained in a memory associated with the programmable controller and selecting the treatment light regimen based on a match.

22. The apparatus of claim 12, wherein the programmable controller is configured to process the measured light received from the output of the one or more sensors and provide a treatment light regimen by matching the measured light received to memory information using artificial intelligence methods and deep learning contained in a memory associated with the programmable controller, and selecting the treatment light regimen based on a match.

* * * * *